(12) United States Patent
Baena Restrepo et al.

(10) Patent No.: US 10,246,547 B2
(45) Date of Patent: Apr. 2, 2019

(54) PROCESSES FOR OBTAINING A POLYOL FROM PALM OIL, POLYOLS OBTAINED FROM THE PROCESSES, PRODUCTS DERIVED FROM SUCH POLYOL AND THEIR METHOD OF PREPARATION

(71) Applicant: INDUSTRIAL AGRARIA LA PALMA LIMITADA, INDUPALMA LTDA., Bogota (CO)

(72) Inventors: Margarita María Baena Restrepo, Medellin (CO); Dency Viviana Agudelo Velásquez, Medellin (CO); Dahiana Toro Álvarez, Medellin (CO)

(73) Assignee: INDUSTRIAL AGRARIA LA PALMA LIMITADA, INDUPALMA LTDA., Bogota (CO)

( * ) Notice: Subject to any disclaimer, the term of this patent is extended or adjusted under 35 U.S.C. 154(b) by 0 days.

(21) Appl. No.: 14/349,029

(22) PCT Filed: Oct. 3, 2012

(86) PCT No.: PCT/IB2012/001954
§ 371 (c)(1),
(2) Date: May 21, 2014

(87) PCT Pub. No.: WO2013/050854
PCT Pub. Date: Apr. 11, 2013

(65) Prior Publication Data
US 2014/0309322 A1    Oct. 16, 2014

(30) Foreign Application Priority Data

Oct. 3, 2011    (CO) .................................. 11130078

(51) Int. Cl.
*C11C 3/06*        (2006.01)
*C08G 18/36*       (2006.01)
(Continued)

(52) U.S. Cl.
CPC ............ *C08G 18/348* (2013.01); *C07C 29/00* (2013.01); *C07C 29/74* (2013.01); *C08G 18/10* (2013.01);
(Continued)

(58) Field of Classification Search
CPC .................................... C11C 3/06; C11C 3/10
See application file for complete search history.

(56) References Cited

U.S. PATENT DOCUMENTS

| | | | | |
|---|---|---|---|---|
| 2,806,046 A | * | 9/1957 | Tess ........................... | C11C 3/04 252/77 |
| 3,424,766 A | * | 1/1969 | Masters ................. | C08G 18/36 106/244 |

(Continued)

FOREIGN PATENT DOCUMENTS

| | | | |
|---|---|---|---|
| CN | 101016225 A | * | 8/2007 |
| SG | 55223 A1 | * | 12/1998 |

OTHER PUBLICATIONS

Derawi, D.; Salimon, J. Optimization on Epoxidation of Palm Olein by Using Performic Acid. E-Journal of Chemistry, 2010, vol. 4, pp. 1440-1448.*

(Continued)

*Primary Examiner* — Stephen E Rieth
(74) *Attorney, Agent, or Firm* — Birch, Stewart, Kolasch & Birch, LLP

(57) ABSTRACT

The present invention relates to the process for production of a polyol from palm oil and of rigid polyurethane foams prepared from said polyol derived from palm oil. On the one hand, this invention provides a method for obtaining monomeric polyols from palm oil that have hydroxyl number between 50 450 mgKOH/g sample. The polyols of the present application may be obtained by means of a procedure based on the following four mother routes: Route 1: maleinisation of the fatty acids of palm oil; Route 2:

(Continued)

Route 4 + Route 2 glycerolysis of palm oil; Route 3: trancesterification of palm oil; and Route 4: epoxidation of unsaturated carbon-carbon links of palm oil. Additionally, other modalities of the invention permit obtaining polyols from the combination of these mother routes. In other realizations of the invention polyurethanes are prepared from polyols obtained through any of the four routes or by combinations of the same.

4 Claims, 5 Drawing Sheets

(51) Int. Cl.
    *C08G 18/34*      (2006.01)
    *C07C 29/00*      (2006.01)
    *C08G 18/80*      (2006.01)
    *C08G 18/10*      (2006.01)
    *C08G 18/32*      (2006.01)
    *C07C 29/74*      (2006.01)
    *C11C 3/02*      (2006.01)
    *C08G 101/00*      (2006.01)

(52) U.S. Cl.
    CPC ......... *C08G 18/3206* (2013.01); *C08G 18/36* (2013.01); *C08G 18/8019* (2013.01); *C11C 3/02* (2013.01); *C11C 3/06* (2013.01); *C08G 2101/0008* (2013.01); *C08G 2101/0025* (2013.01); *C08G 2101/0083* (2013.01)

(56) References Cited

U.S. PATENT DOCUMENTS 5,543,472 A * 8/1996 Stevens .................. C08C 19/06
                                                          525/331.9
2010/0261805 A1* 10/2010 Abraham et al. ............. 521/170

OTHER PUBLICATIONS

Columbia University: Intensive Seminars in Modern Chemistry. Experiment 3: Liquid-liquid Extraction and Recrystallization. http://www.columbia.edu/cu/chemistry/ugrad/hssp/EXP_3.html. As viewed on Feb. 14, 2008 (Wayback Machine).*

Campanella, A.; Baltanas, M. A. Degradation of the oxirane ring of epoxidized vegetable oils in liquid-liquid systems: I. hydrolysis and attack by H2O2. Latin American Applied Research, 2005, vol. 35, pp. 205-210.*

PGEO Group: Our Products—Palm Oil Products. http://www.pgeogroup.com.my/products01.htm. As viewed on Oct. 21, 2015.*

Definition of dry. Dictionary.com. http://www.dictionary.com/browse/dry. As viewed on Mar. 28, 2016.*

Fats, Oils, Fatty Acids, Triglycerides. Scientific Psychic. http://www.scientificpsychic.com/fitness/fattyacids1.html. As viewed on Jun. 15, 2016.*

Machine Translation of CN101016225A. Aug. 15, 2007. (Year: 2007).*

Sonntag, N. O. V. Glycerolysis of Fats and Methyl Esters—Status, Review and Critique. Journal of the American Oil Chemists Society. 1982, vol. 59, pp. 795A-802A. (Year: 1982).*

* cited by examiner

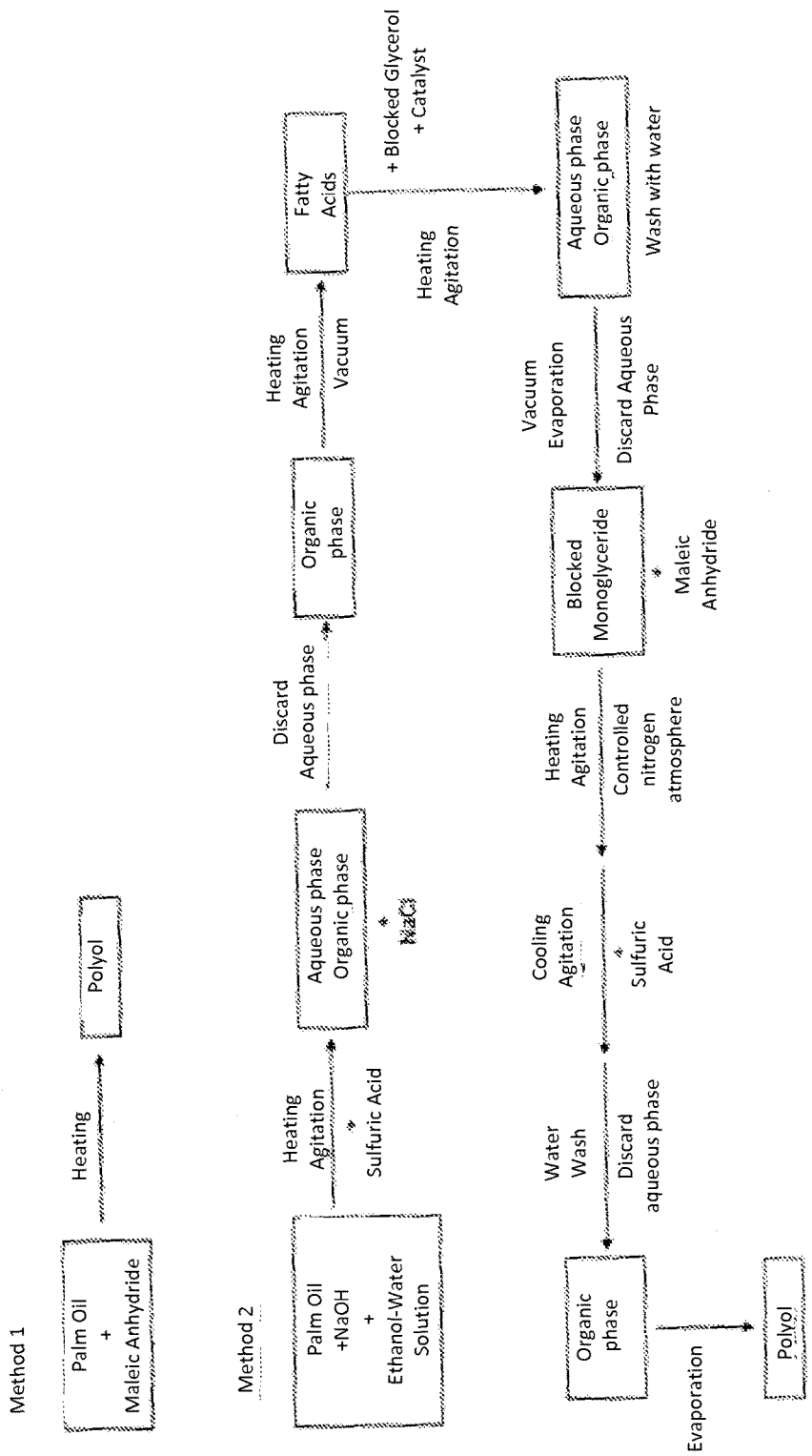
FIG. 1 — Route 1: Maleneisation of palm oil and Maleinisation of fatty acids

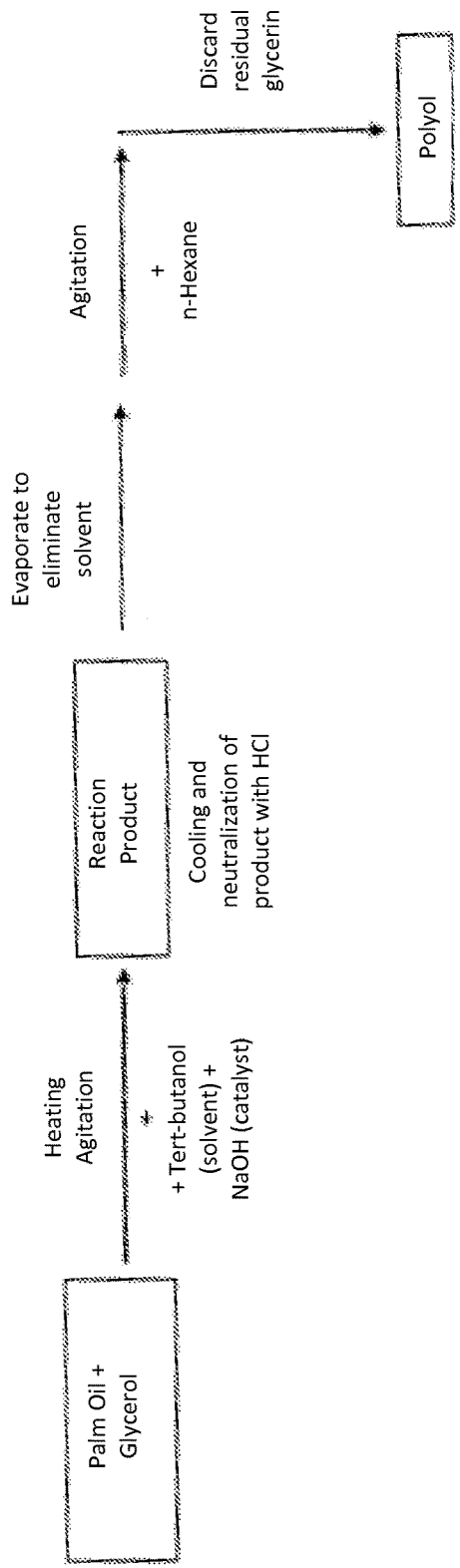
FIG. 2 – Route 2: Glyceroysis of palm oil

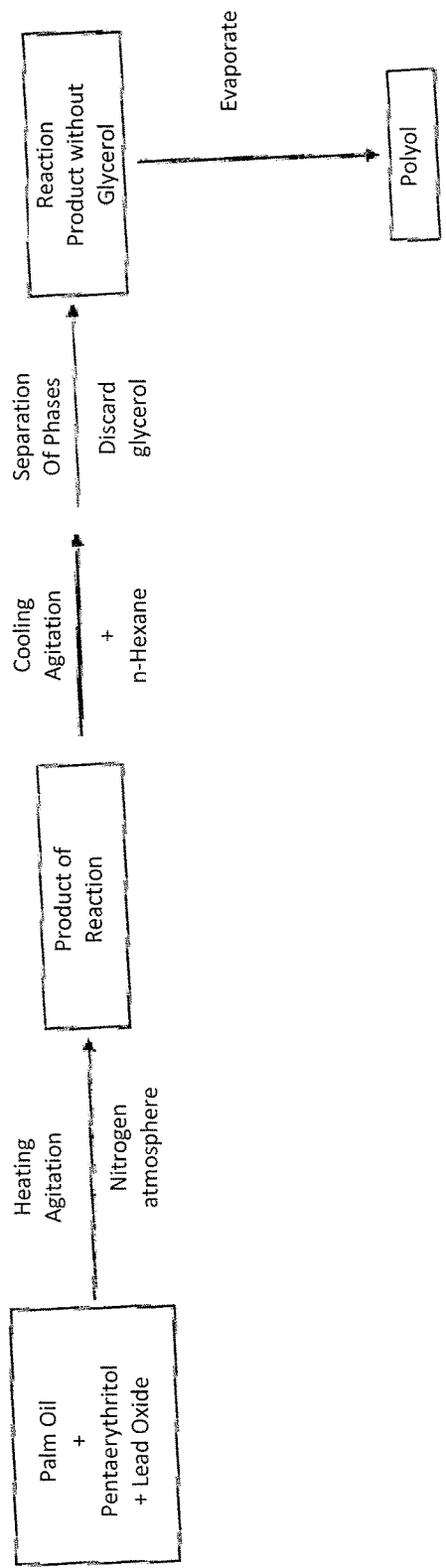
FIG. 3 – Route 3: Transesterification with pentaerythritol

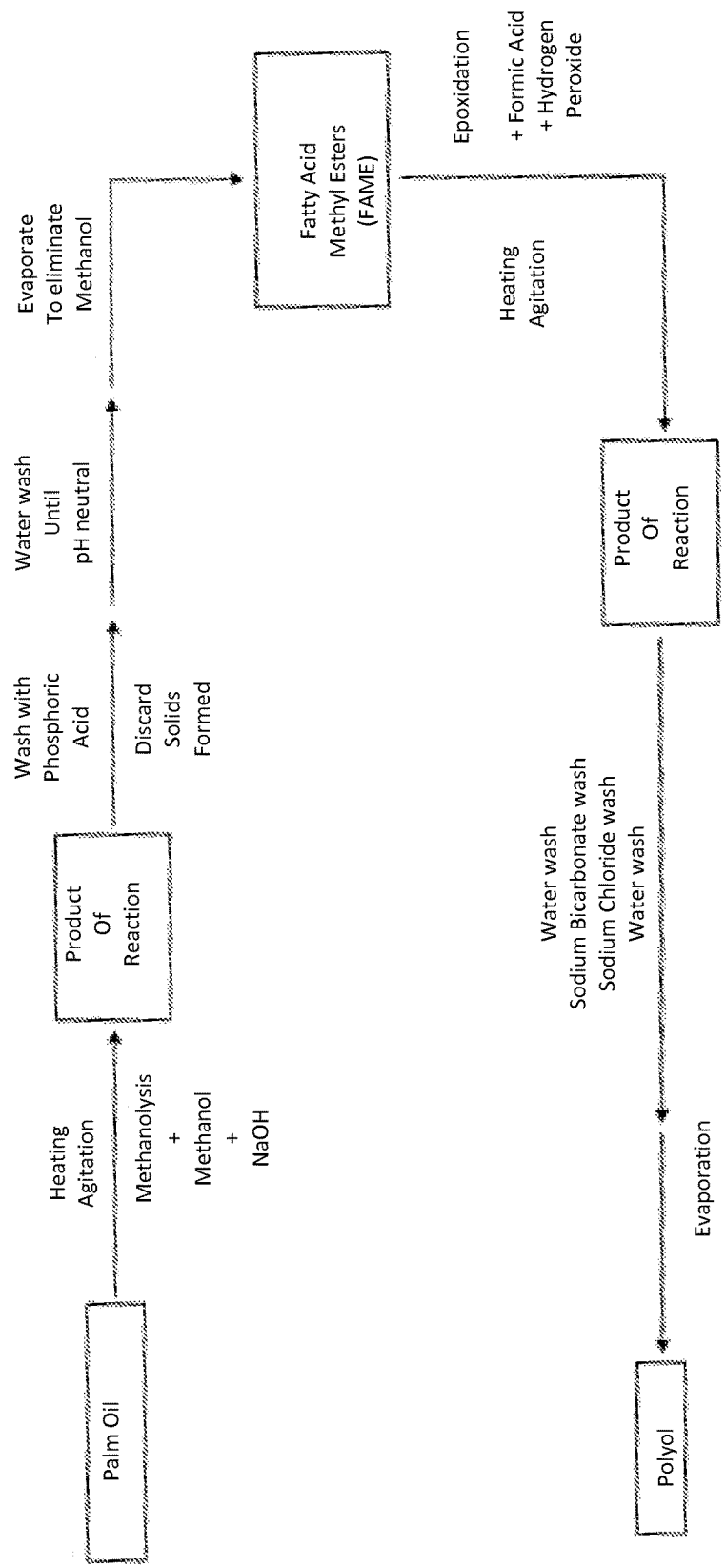
FIG. 4 – Route 4: Epoxidation of the double bond

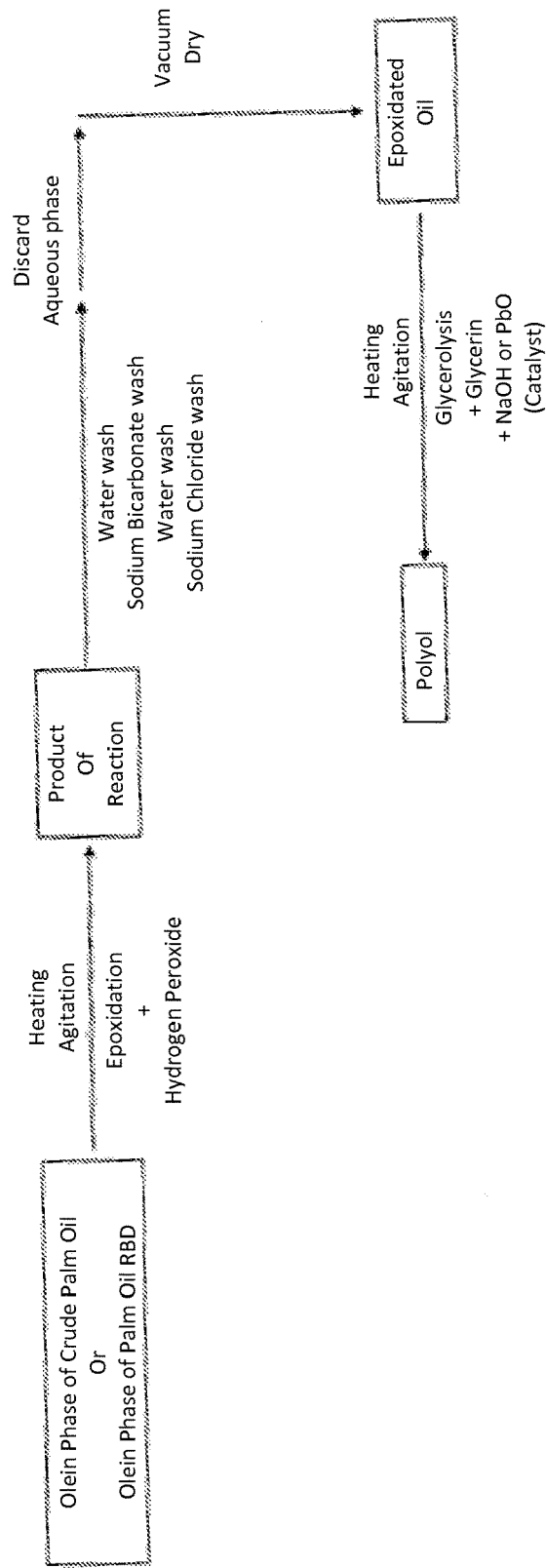
FIG. 5 – Route 4 + Route 2

PROCESSES FOR OBTAINING A POLYOL FROM PALM OIL, POLYOLS OBTAINED FROM THE PROCESSES, PRODUCTS DERIVED FROM SUCH POLYOL AND THEIR METHOD OF PREPARATION

FIELD OF THE INVENTION

Synthetic polymers were invented about 60 years ago and from then on much progress has been achieved in the field of their applications. Polyurethane is a polymer obtained through condensation of polyols combined with polyisocyanates. It is subdivided in two major groups: thermostables and thermoplastics. The more usual thermostable polyurethanes are foams frequently used as thermal insulators and as resilient foams, but there are also polyurethanes that are high performance elastomers, adhesives and sealants, paints, fibers, packaging sealants, joints, preservatives, automobile components, elements in the construction industry, furniture industry, and other multiple applications.

Polyols used in the production of polyurethanes are generally compounds with molecular weight in the range of 500 to 5000 g/mol. Depending of the length of the chain of these diols and glycols, the properties of the polyurethanes change. If the polyol has a low molecular weight, it makes rigid plastics, and if it has a high molecular weight it produces flexible elastomers. Polyols are reactive substances, usually liquids, which contain at least two groups that react to isocyanate linked to one molecule. They have a deep effect in the properties of finished polyurethane. The properties of the polymers are associated with the links to isocyanate, but the structure of polyol exercises a direct action on the processing and finishing properties of the polymer.

BACKGROUND OF THE INVENTION

The polyols used in the polyurethane production industry are generally derived from petroleum, but currently there is a trend to use renewable sources such as vegetable oils for production of polyols based on these oils.

The production of polyols from of vegetable oils has been described in several documents in the state of the art:

Patent Application U.S. 20070232816 reveals a process for the production of a polyol monomer which consists of reacting an unsaturated acid fatty or its corresponding triglycerides with a polyhydric alcohol in the presence of a catalyst and an emulsifier in order to prepare a monoglyceride. Said process also comprises an epoxidation stage of the unsaturated fatty acids of said monoglyceride, and a reaction stage of the epoxidized monoglyceride with a polyhydric alcohol.

Publication W0/2006/012344 provides methods for the preparation of unsaturated polyols based one modified vegetable oils, as well as methods for the production of oligomeric polyols based on modified vegetable oils. This publication shows a method of manufacturing an oligomeric polyol based on a modified vegetable oil, where a mixture is made to react that comprises an epoxidized oil vegetable and a compound that allows the opening of the ring for form an oligomeric polyol based on the modified vegetable oil, where the oligomeric polyol based on the modified vegetable oil comprises at least 20% of oligomers and has a viscosity at 25° C. less than approximately 8 Pa s.

Publication W0/2009/058367, as well as Publication W0/2009/058368 refer to methods for obtaining a polyester polyol from natural oils. Such methods comprise the stage of reacting the monohydric fatty acids to the esters with a multifunctional reagent initiator to form the polyester polyol. This document reveals a process where a methanolysis of oils (Sunflower, Soya, Canola) is performed followed by an epoxidation process.

U.S. Pat. No. 6,433,121 reveals a method for the production of polyols based on natural oils through the use of a two consecutive-stage process involving epoxidation and hydroxylation. This document mentions in a general manner that palm oil may be used; however, without limitation, the preferred realization of the invention corresponds to the use of soybean oil.

Publication W0/2009/058368 reveals methods for the obtaining a polyester polyol from natural oils. Said method comprises a stage of reacting the hydroxylated fatty acids to the esters with a reagent multifunctional initiator to form polyester polyol. The process revealed in this document performs a methanolysis of oils (Sunflower, Soya, Canola) followed by a process of epoxidation. Additionally, the document mentions in a general way that palm oil could be employed in the process.

In the research published in the Article by G. Ruiz Aviles, "Obtaining and characterizing of a biodegradable polymer from Cassava starch," *Engineering and Science*, Medellin, 2006, a biodegradable polymer is obtained from yucca starch by processing modified starch mixtures with glycerin and water as plasticizers, using an open mill and a single extruder spindle. The variables to control during the extrusion are: temperature, torque and spindle rotation speed profile. The polymer obtained has applications in food packaging and for garbage bags.

On the other hand, the article by H. Yeganeh, P. et al., "Preparation and properties of novel biodegradable polyurethane networks based on castor oil and poly(ethylene glycol)," *Polymer Degradation and Stability* 92, Iran, 2007, reveals a method of preparation of polyurethane with polyols obtained from castor oil and mixtures with polyethylene glycol that were synthesized through the reaction of the prepolymer with 1,6 hexamethylene diisocyanate. The polymer obtained has a rate of biodegradability compatible for be used in biomedical applications.

The article by S. Ahmad, Md, et al., "Urethane modified boron filled polyesteramide: a novel anti-microbial polymer from a sustainable resource," *European Polymer Journal*, 2004 describes a procedure for obtaining an antimicrobial polymer from soybean oil; the polymer is composed of polyesteramide filled with boron that is polymerized for form a polyester amide urethane. The material obtained was evaluated for antimicrobial and antifungal activity, verifying that the different compositions inhibit microbial growth.

Another article, by V. Sharma, et al., "Addition polymers from natural oils: A review," *Prog Polym. Sci.* 31, India, summarizes the theoretical aspects of the production of polymers from renewable sources, especially from vegetable oils, showing the differences in the structure of each oil and its influence on the polymer properties. It poses various alternatives for natural oils such as soy, corn, tung, linseed, castor oil plant and fish oil for the production of polymer materials.

Finally, the article by G. Gunduzb, et al., "Water-borne and air-drying oil-based resins," *Progress in Organic Coatings* 49, Turkey 2003, presents a procedure for the preparation of polyurethane dispersed in water for application as a varnish. The resin is produced for the preparing a maleinised monoglyceride, TDI as isocyanate, silicone, and ethylene diamine. Sunflower oil was used for this development as a renewable resource to produce the monoglycerides.

Palm oil is the second most cultivated vegetable oil in the world following soybean oil. Ninety percent of palm oil produced is exported from Malaysia and Indonesia. Palm oil is derived from the fruits clusters of the palm, is semisolid at environmental temperature due to the combination of triglycerides of high and low fusion points, and has a red-orange color due to its high content of carotenes. It is composed mainly of fatty acids, the amounts typical of these acids being: 45% palmitic, 40% oleic, 10% linoleic and 5% stearic. Thanks to its good resistance to oxidation and to heating at high temperatures, palm oil is employed in diverse industries for its good performance and economy. In energetic terms palm oil requires less energy than others oils for the production of one ton, such as soy and rapeseed oils.

Initially palm oil production was only used for human consumption, but in view of the overproduction of palm oil of in Malaysia, Thailand and Indonesia, the need to search for alternative uses for the oil has been identified. Some different areas of knowledge have been identified for its use, such as medicine, agriculture development of new materials, civil works, and biofuels, among others.

The production of polyols to from of palm oil, specifically oligomeric polyols, has been described in Publication W0/2007/123637, which discloses oligomeric polyols obtained from palm oil and compositions that comprise these polyols, as well as a process for obtaining an oligomeric polyol based on modified palm oil, which comprises providing an epoxidized composition based on palm oil and making it react with a compound that allows the opening of the ring to form an oligomeric polyol where the oligomeric polyol based on the modified palm oil comprises at least 40% oligomers by weight, has a hydroxyl number of around of 65 mg KOH/g sample or less, an average number of hydroxyl functionality of 2.5 or less, and viscosity at 25° C. of less than approximately 4 Pa s.

While the prior art has searched for solutions to the technical problem, which is to provide methods for obtaining "green" polyols, that is, from vegetable oils which include palm oil, as well as obtaining polyurethane foams from of these "green" polyols with properties that allow their application in the different uses mentioned above, none of the documents of the prior art refers to a procedure for obtaining polyols derived from palm for the preparation of polyurethane, in which two methods of preparation are combined to grant a higher functional ty to the final molecular structure. This improves the characteristics of the polyurethane obtained from said polyol, conferring properties such as greater functionality and greater crosslinking.

Although in other inventions polyols have been obtained from vegetable oils, the products prepared from such polyols are brittle due to the concentration of hydroxyl groups at only one end of the carbon chain.

Additionally and in relation to the conditions of operation of the glycerolysis method, the present invention achieved decreasing the reaction temperature for obtaining a polyol with favorable results regarding the decrease in energy costs.

The present invention provides a simple method for its realization, is not expensive, and gives the end result of a product with high technical and functional qualities that places it above those of conventional type and within the same line found in the prior art, with the advantage of having in its raw materials a polyol from renewable natural sources.

The present invention produces polyols with molecular weights between 314 and 3366 and with a hydroxyl number of between 50 and 450 mg KOH/g sample.

The resulting rigid foams were tested for the density (according to STM C373-88) with results between 0.284 and 0.658 g/cm$^3$, Young module (according to ASTM 0695-10) with results between 8.94522 and 54.92330 MPa, and maximum effort (according to ASTM 0695-10) with results between 0.92037 and 8.29101 MPa.

The resulting semi-rigid foams were tested for density (according to ASTM C373-88) with results between 0.129 and 0.158 g/cm3, Young module (according to ASTM 0695-10) with results between 0.78727 and 1.54311 MPa, and maximum effort (according to ASTM 0695-10) with results between 0.07012 and 0.09753 MPa.

DESCRIPTION OF THE INVENTION

The present invention is related to the production process of a polyol from palm oil and to rigid polyurethane foams prepared from said polyol derived from palm oil.

On the one hand, the present invention provides a method for obtaining monomeric polyols from palm oil that have a hydroxyl number of between 50 450 mgKOH/g sample.

The polyols of the present application may be obtained by means of a procedure based on the following four mother routes:

Route 1: maleinization of the fatty acids of palm oil
Route 2: glycerolysis of palm oil
Route 3: transesterification of palm oil
Route 4: epoxidation of unsaturated carbon-carbon bonds in palm oil Additionally, other modalities of the invention allow the obtaining polyol from the combination of these mother routes.

Specifically, route 1 begins with the alcoholysis of palm oil to obtain fatty acids, which undergo a maleinization process in order to introduce carboxylic groups and from these to extend the glycerin chain and so obtain a polyol from palm oil.

In the mother route 2 of the present invention monoglycerides are prepared from the palm oil but, in contrast to route 1, no maleinization is performed. Rather, polyol is obtained from the palm oil by means of glycerolysis process. The glycerolysis takes place at temperatures between 170 and 280° C., obtaining higher reaction speeds the higher the temperature. It is recommended not to exceed 260° C. in any case, provide a good system of agitation (350 to 420 rpm) and use an inert atmosphere (Nitrogen, argon or CO2).

The process of glycerolysis is usually performed in presence of a solvent and a catalyst. The selection of a good catalyst allows using lower temperatures.

The glycerolysis reaction should be carried out under the action of a catalyst that can be homogeneous (acid or base) or heterogeneous. Examples of the catalysts to obtain mono and di glycerides include lead acetate, calcium acetate, lead oxide and lithium ricinoleate, sulfuric acid, hydrochloric acid, sulfonic acid and sodium hydroxide.

Lead and calcium acetates, as well as the lithium ricinoleate, allow obtaining an excellent glycerolysis in the minimum time (40 to 50 minutes) and relatively moderate temperature (235 to 240° C.) and, more importantly, using minimum amounts of catalyst.

The mother route 3 of the present invention corresponds to the preparation of a polyol from palm oil modified through transesterification with pentaerythritol, which is useful when a considerable increase in tensile, hardness and resistance to chemical attack properties is required. This is due to a higher degree of crosslinking caused by the increase in the content of hydroxyl groups.

In mother route 4 of the present invention a polyol to from palm oil is produced by double link epoxidation, in which a process of methanolysis of the palm oil is initially performed to obtain of fatty acid methyl esters (FAME), which are submitted to a process of epoxidation with hydrogen peroxide to generate performic acid in situ.

In other aspect of the invention polyurethanes are prepared from the polyols obtained through any of the four routes or through a combination of the same. In a modality of the invention, the polyurethanes are produced through the reaction of a mixture of polyol obtained through the present invention, a commercial polyol, a surfactant, a catalyst and an isocyanate. The polyurethanes may be foams of high density rigid polyurethane.

In one embodiment of the present invention, a method for the production of polyol from palm oil is characterized by the following steps: a) mix a source of palm oil with formic acid in the presence of heat; b) add hydrogen peroxide to the mixture of step a) and shake to obtain a reaction product of step b); c) wash the reaction product of step b) with water at a temperature between 55° C. and 65° C. to obtain a product of step c); d) wash the product obtained in the step c) with 5% sodium bicarbonate to obtain a product of reaction of step d); e) wash the product of reaction of step d) with water at a temperature between 55° C. and 65° C. to obtain a product of step e); f) wash the product obtained in step e) with 5% sodium chloride to obtain an aqueous phase and an organic phase; g) discard the aqueous phase obtained in step f) to obtain an epoxidized oil; h) dry to remove the organic phase remaining of step f); and i) mix the epoxidized oil obtained in step g) with glycerol and catalyst, in the presence of heat and agitation. In another embodiment of the present invention, step b) has a reaction temperature that varies between 45° C. and 55° C. and has a time that varies between 1 and 2 hours after the addition of hydrogen peroxide. In yet another embodiment of the present invention, step i) has a reaction temperature that varies between 170° C. and 190° C. and has a time of reaction that varies between 40 and 50 minutes.

The specific characteristics, advantages and novel characteristics of this invention will be established in the following section of the description, corresponding to the detailed description of the invention.

BRIEF DESCRIPTION OF THE DRAWINGS

FIG. 1 shows a flow chart exemplifying the production of a polyol from palm oil through Route 1.

FIG. 2 shows a flow chart exemplifying the production of a polyol from palm oil through Route 2.

FIG. 3 shows a flow chart exemplifying the production of a polyol from palm oil through Route 3.

FIG. 4 shows a flow chart exemplifying the production of a polyol from palm oil through Route 4.

FIG. 5 shows a flow chart exemplifying the production of a polyol from palm oil through the combination of Route 4 and Route 2.

DETAILED DESCRIPTION THE INVENTION

The present invention relates to a process for the production of a polyol from palm oil and of rigid polyurethane foams with a polyol derived from palm oil mixed with a commercial polyol.

The processes for the production of the polyols based on palm oil will be described by referring to FIGS. 1 to 5.

FIG. 1 describes route 1 in a general manner. Specifically, this route includes two different methods, the first comprising the maleinization of palm oil through heating of the same and its mixture with maleic anhydride. The mixture is later reacted in the presence of reflux condenser and an inert atmosphere, and the reaction happens there during an established period, obtaining the polyol.

The second method corresponds to the maleinization of fatty acids, beginning with a mixture of palm oil and sodium hydroxide and an ethanol-water solution. The mixture obtained is heated and stirred. Subsequently a small amount of concentrated sulfuric acid is added, showing the separation of the organic phase and the aqueous phase.

Then, saturated sodium chloride solution is added. After of the complete separation of the phases, the aqueous phase is eliminated. By means of warming and agitation of the organic phase the fatty acids may be obtained, which are mixed with previously blocked glycerol through an MEK (Methyl ethyl ketone) reaction, carried out with sulfonic toluene acid as a catalyst and toluene as a solvent. The fatty acids then react with the glycerol blocked in the presence of a catalyst, sulfonic toluene acid, and heat. The product of this reaction is evaporated to obtain blocked monoglyceride, which subsequently reacts in a nitrogen and maleic anhydride atmosphere. Sulfuric acid is added to the product of this reaction. The organic phase obtained is washed and submitted to evaporation to finally obtain the polyol.

Now thus, FIG. 2 summarizes route 2 which corresponds to the production of polyol from palm oil through glycerolysis. This route comprises the reaction between the palm oil and glycerol, terbutanol as a solvent and sodium hydroxide as a catalyst in the presence of heat. The product of this reaction is neutralized with hydrochloric acid and submitted to evaporation for elimination of the solvent. The phase obtained is separate through the addition of n-hexane, allowing the residual glycerin to be discarded from the polyol finely obtained.

FIG. 3 summarizes route 3, related to the production of polyol from palm oil modified through transesterification with pentaerythritol. This route comprises the reaction between palm oil, pentaerythritol and lead oxide in the presence of heat with continuous agitation and in an inert nitrogen atmosphere. The product of the reaction is treated with n-hexane, allowing formation of two phases: the precipitate that contains glycerol is then discarded and the other phase is submitted to evaporation to obtain the polyol.

On the other hand, route 4 is summarized in FIG. 4 and comprises a process of epoxidation of the fatty acid methyl esters of (FAME), which are previously obtained through methanolysis of palm oil. This methanolysis comprises the reaction between the palm oil and methanol in presence of sodium hydroxide. Subsequently the glycerin phase is discarded and the phase of interest is washed with phosphoric acid, discarding the solids formed and neutralizing. The product (FAME) is submitted to evaporation to remove the excess methanol.

In this way, the FAME are made to react with formic acid in the presence of hydrogen peroxide. The reaction is evidenced by the color change from orange to clear yellow. Subsequently, the product is washed with water, sodium bicarbonate and sodium chloride, neutralizing the solution, which then undergoes evaporation to remove the moisture and allow obtaining the polyol.

FIG. 5 describes other modalities of the invention, which correspond to the combination of routes 2 and 4 and are established in more detail below.

One of these modalities allows obtaining polyol from of the olein phase of crude palm oil, using lead oxide as a catalyst. The method is then carried out through the epoxidation of the olein phase of crude palm oil with formic acid, in the presence of heat. Subsequently hydrogen peroxide is added and stirred. The reaction is evidenced by the change of color from orange to clear yellow. The product of the reaction is washed with water, sodium bicarbonate and sodium chloride, discarding the aqueous phase and subjecting the organic phase to glycerolysis (reaction with glycerin) using lead oxide as catalyst to thus obtained the polyol.

Another mode of the invention corresponds to obtaining the polyol from the olein phase of crude palm oil using NaOH as a catalyst. This mode comprises the same steps mentioned for the previous mode, with the difference that the glycerolysis of the organic phase is done in the presence of sodium hydroxide, with a posterior neutralization of the excess catalyst with phosphoric acid.

Yet another mode of the invention allows obtaining polyol from the olein phase of refined, bleached and deodorized palm oil (RBD). For this purpose the same steps are used as for the previous embodiments, using the raw material mentioned and sodium hydroxide as a catalyst in the glycerolysis.

The last mode corresponds to obtaining polyol from of the olein phase of refined, bleached and deodorized palm oil (RBD), but employing lead oxide as catalyst. In the same way, the steps already mentioned above are used, with the exception that the olein phase of RBD is used as raw material and lead oxide as catalyst in the glycerolysis.

The routes and modalities described thus allow obtaining the polyurethane foams through the reaction of the polyols produced with methylene diphenyl diisocyanate (MDI).

For said purpose, the polyol obtained is mixed with a short chain polyol (diethylene 1,6 butanediol), a catalyst (dibutyltin dilaurate, tin octoate, tertiary amine catalysts, water, a surfactant (Silicone or organosiloxane-based), and methylene diphenyl diisocyanate (MDI). The reaction leads to the formation of foam of rigid polyurethane.

Depending on the hydroxyl number obtained for the polyol, flexible, semi-rigid and rigid polyurethane foams may be obtained, as indicated below:

| | Hydroxyl No. | | | | | | |
|---|---|---|---|---|---|---|---|
| 50 | 100 | 150 | 200 | 250 | 300 | 350 | 400 |
| Foam Type | Flexible | | Semi-rigid | | | Rigid | |

Within of the applications that these types of foam have, the following may be noted:

| Polyurethane | Application |
|---|---|
| Rigid | Molded parts, soles for footwear |
| Semi-rigid | Thermal insulation, soundproofing insulation, waterproofing, floral foam, chairs adapted to the user (mainly for disabled people) |
| Flexible | Foam for bras, mattresses |

EXAMPLES

The following examples is presented with the purpose of illustrating the invention and are in no way a limitation, inasmuch as the person moderately skilled in the matter can recognize the possible variations.

Example 1—Obtaining Polyol Using the First Method of Route 1

300 grams of palm oil were laced in the 250 ml reaction flask. Separately, 65.7 grams of maleic anhydride were weighed and were added to the reaction flask. The same was heated to 180° C. Subsequently the reflux condenser was adapted and the reaction flask placed on a heating iron with magnetic agitation to 1300 allowing the reaction to take place during 3 hours in a low nitrogen atmosphere. The product of this reaction is the maleinised oil that was cooled to the 100° C. and to which an amount of 30.85 g of glycerol was added. The reaction was allowed to continue and the acidity index tracked every 30 minutes up to a value of 90 mg KOH/g sample, thus obtaining the polyol.

Example 2—Obtaining Polyol Using the Second Method of Route 2

150 grams of palm oil were placed in a 1000 ml precipitation glass. Subsequently 33.5 g of NaOH and 100 ml of a 1:1 ethanol-water solution were added. The reaction was carried out at a temperature of 80° C. during 30 minutes. The solution was stirred slightly in manual form. Then, drops of concentrated sulfuric acid were added. The separation of the organic phase and the aqueous phase was then observed. To complete the solution, 100 ml of saturated sodium chloride solution were added. The solution was left at rest while the phases separated. Subsequently the aqueous phase was discarded and is the rest transferred to a separation funnel, washing with hot water. The pH of discarded wash water was measured to verify it was neutral. Separately, the organic phase was transferred to an lateral release Erlenmeyer, the temperature was increased to 80° C., and the phase was stirred continuously; This procedure was carried out in a vacuum. The fatty acids were obtained as a product.

70.83 grams of glycerol were separately weighed and placed in a 500 ml reaction flask. Then 62.90 grams of MEK (methyl ethyl ketone) were added together with 1.8 grams of sulfonic toluene acid and 70 ml of toluene. The reaction was carried out at 90° C. during 2 hours. In this way the blocked glycerol was obtained.

To 40 grams of the fatty acids obtained above, 19.5 grams of blocked glycerol were added in a 500 ml reactor. Subsequently 1.8 grams of sulfonic toluene acid were added and the remaining solution underwent heating at 90° C. with magnetic agitation of 1200 rpm, leaving the reaction to develop for three and a half hours. Then the product of the reaction was moved to a separation funnel, also washing with hot water and measuring the pH of outgoing wash water until it was neutral. The product of this washing is consecutively put under rotoevaporation during 3 hours at a temperature of 90° C. and in vacuum conditions. By these means the blocked monoglyceride was obtained. Afterwards 25 grams of the blocked monoglyceride are taken and placed in a 500 ml reaction flask. Subsequently 9.2 grams of maleic anhydride are added and the reaction is carried out at 200° C. with magnetic agitation during 3 hours in a low nitrogen atmosphere. The product is left to cool to 100° C. without stopping the agitation. Four drops of concentrated sulphuric acid are immediately added slowly, dissolved in 3 ml of distilled water, and the reaction is allowed for another hour. A hot water wash is then carried out and the result left decanting throughout the night.

The following day is the aqueous phase was discarded and the organic phase was rotoevaporated at 80° C. during an hour and a half, thus obtaining the polyol.

Example 3—Obtaining Polyol Using Route 2

In a 500 ml reaction flask, coupled with a reflux condenser, a heating surface and a magnetic agitator, 64.5 grams of palm oil were added, along with 40 grams of glycerol, 20 ml of terbutanol and 4.5 grams of sodium hydroxide. The conditions of operation were, temperature: 90° C., time: 2 hours and agitation: 1300 rpm.

Once the time of reaction had elapsed the mixture was cooled to temperature and the catalyst neutralized with an HCl solution at 10%, verifying the pH with a paper indicator. The glycerin and the residual solvent were then removed and the product of interest was rotoevaporated to ensure the complete elimination of solvent in the solution. The rotoevaporation temperature was 90° C. and was carried out during 3 hours.

Finally the phases were separated in a separation funnel, where 60 ml of n-hexane were added with vigorous stirring and constant releasing of pressure. The result was left in repose and the bottom phase discarded, which contained residual glycerin. A polyol was obtained with a hydroxyl number value of 523.23 mg KOH/g sample.

Example 4—Obtaining Polyol Using Route 3

In a 500 ml reaction flask 40.0 grams of palm oil were weighed, along with 4.32 grams of pentaerythritol and 0.02 grams of lead oxide. Subsequently, the flask was placed on a heating surface where the mixture remained in reaction at a temperature of 200° C., with continuous agitation, an inert atmosphere of nitrogen and water reflux condenser during 2 hours. It was then left to cool and 40 ml of n-hexane were added in a separation funnel, stirring and releasing pressure. The phases were allowed to separate to further discard the precipitate and the glycerol. The other phase was submitted to rotoevaporation at 70° C. with constant agitation for 3 hours, thus obtaining the polyol, with a hydroxyl number value of 11.86 mg KOH/g sample.

Example 5—Obtaining Polyol Using Route 4

Initially the methanolysis of palm oil was carried out, in a 500 ml reaction flask, taking 500 grams of palm oil, together with 160.8 g of methanol and 9 grams of sodium hydroxide. The mixture was carried out at a temperature of 70° C. with agitation of 1000 rpm during 1 and a half hours.

After the reaction time, the product was taken to a separation funnel to discard the glycerin phase that was in the bottom. The phase of interest was then washed with 100 ml of 0,015N phosphoric acid at 60° C., the solids formed were discarded, and repeated the wash was repeated with water at 60° C. until the pH was neutralized. The phase of interest was then submitted to rotoevaporation during 3 hours at a temperature of 80° C., for removal of excess methanol. The product obtained corresponds to the fatty acid methyl esters (FAME).

Separately, in a 1000 ml reaction flask, 190 grams of FAME were added along with 7.71 grams of formic acid. The mixture was heated at 40° C. and agitated at 800 rpm.

20.85 grams of hydrogen peroxide were then added drop by drop during 1 hour. After the addition of hydrogen peroxide, the reaction continued during 11 hours with constant temperature and agitation. The evidence of the reaction was seen in the change of color from orange to clear yellow. Hot water washes were immediately conducted with until the pH increased to 5. Then a washing with 100 ml of bicarbonate sodium solution at 5% and sodium chloride at 5% was performed. The process ended with hot water washes until completely neutralized.

The resulting mixture was rotoevaporated during 4 hours at 90° C. to remove moisture. The polyol was obtained.

Example 6—Obtaining Polyol Using Routes 2 and 4 (Epoxidation and Glycerolysis) from the Olein Phase of Crude Palm Oil and Using Lead Oxide as Catalyst 200 grams of the olein phase of crude palm oil and 9.97 grams of formic acid were placed in a 500 ml reaction flask, coupled with a reflux condenser, a heating surface to achieve a temperature of 50° C., and magnetic agitation to 800 rpm. The reaction was started and 22.11 grams of hydrogen peroxide were added drop by drop, with agitation constant during 90 minutes. The reaction was allowed to continue during 2 hours. The formation reaction of epoxidized oil was evidenced by a change of color from orange to clear yellow.

Hot water washes were then is conducted until a pH close to 5. A wash was performed with a solution of 5% sodium bicarbonate and with a 5% sodium chloride solution. The aqueous phase was discarded through a separation funnel of and the organic phase transferred to a lateral release Erlenmeyer, drying in a vacuum during 3 hours at 80° C. The glycerolysis was then carried out with 100 grams of epoxidized oil, 25.72 grams of glycerin and 0.03 grams of PbO in a 500 ml reaction flask coupled with a reflux condenser, temperature at 215° C., and agitation of 1300 rpm during 45 minutes. The polyol obtained was analyzed, resulting in hydroxyl numbers of between 60 and 110 mg KOH/g sample.

Example 7—Obtaining Polyol Using Routes 2 and 4 (Epoxidation and Glycerolysis) from of the Olein Phase of Crude Palm Oil and Using Sodium Hydroxide as Catalyst 200 grams of the olein phase of crude palm oil and 9.97 grams of formic acid were placed in a 500 ml reaction flask coupled with a reflux condenser, a heating surface to reach a temperature of 50° C. and magnetic agitation to 800 rpm. The reaction was initiated and 22.11 grams of hydrogen peroxide were added drop by drop, with constant agitation during 90 minutes. The reaction continued during 2 additional hours. The reaction of formation of epoxidized oil was evidenced by a change of color from orange to clear yellow.

Hot water washes were then carried out up to a pH close to 5. A wash was performed with a of 5% sodium bicarbonate solution and with a 5% sodium chloride solution. The aqueous phase was discarded through a separating funnel and the organic phase was transferred to a lateral release Erlenmeyer, drying in a vacuum during 3 hours at 80° C. Subsequently the glycerolysis was performed with 100 grams of epoxidized oil, 25.72 grams of glycerin and 1 gram of NaOH in a 500 ml reaction flask coupled with a reflux condenser, temperature of 180° C. and agitation at 1300 rpm for 45 minutes.

The catalyst was neutralized with drops of phosphoric acid, thus avoiding the formation of soaps. Finally, the polyol obtained was analyzed. It yielded hydroxyl numbers between 400 and 440 mg KOH/g sample.

Example 8—Obtaining Polyol Using Routes 2 and 4 (Epoxidation and Glycerolysis) from the Olein Phase of Refined Bleached Deodorized Crude Palm Oil and Using Sodium Hydroxide as Catalyst 200 grams of the olein phase of crude palm oil and 9.97 grams of formic acid were placed in a 500 ml reaction flask, coupled with a reflux condenser, a heating surface to achieve a temperature of 50° C., and magnetic agitation to 800 rpm. The reaction was initiated and 22.11 grams of hydrogen peroxide were added drop by drop, with constant agitation during 90 minutes. The reaction continued during 2 additional hours. The reaction of formation of epoxidized oil was evidenced by a change of color from orange to clear yellow.

Hot water washes were then carried out up to a pH close to 5. A wash was performed with a of 5% sodium bicarbonate solution and with a 5% sodium chloride solution. The aqueous phase was discarded through a separating funnel and the organic phase was transferred to a lateral release Erlenmeyer, drying in a vacuum during 3 hours at 80° C. Subsequently the glycerolysis was performed with 100 grams of epoxidized oil, 25.72 grams of glycerin and 1 gram of NaOH in a 500 ml reaction flask coupled with a reflux condenser, temperature of 180° C. and agitation at 1300 rpm for 45 minutes.

The catalyst was neutralized with drops of phosphoric acid, thus avoiding the formation of soaps. Finally, the polyol obtained was analyzed. It yielded hydroxyl numbers between 370 and 420 mg KOH/g sample.

Example 9—Obtaining Polyol Using Routes 2 and 4 (Epoxidation and Glycerolysis} from the Olein Phase of Refined Bleached Deodorized Crude Palm Oil and Using Lead Oxide as Catalyst 200 grams of the olein phase of crude palm oil and 9.97 grams of formic acid were placed in a 500 ml reaction flask, coupled with a reflux condenser, a heating surface to achieve a temperature of 50° C., and magnetic agitation to 800 rpm. The reaction was initiated and 22.11 grams of hydrogen peroxide were added drop by drop, with constant agitation during 90 minutes. The reaction continued during 2 additional hours. The reaction of formation of epoxidized oil was evidenced by a change of color from orange to clear yellow.

Hot water washes were then carried out up to a pH close to 5. A wash was performed with a of 5% sodium bicarbonate solution and with a 5% sodium chloride solution. The aqueous phase was discarded through a separating funnel and the organic phase was transferred to a lateral release Erlenmeyer, drying in a vacuum during 3 hours at 80° C. Subsequently the glycerolysis was performed with 100 grams of epoxidized oil, 25.72 grams of glycerin and 0.3 grams of PbO in a 500 ml reaction flask coupled with a reflux condenser, temperature of 180° C. and agitation at 1300 rpm for 45 minutes.

Finally, the polyol obtained was analyzed. It yielded hydroxyl numbers between 80 and 90 mg KOH/g sample.

Example 10—Preparation of a Polyurethane Varnish from Polyol Obtained by Route 1 of the First Method The pre-polymer was formed taking 30 g of polyol, 76.92 g surfactant and 20 ml of MEK (Methyl ethyl ketone) in a 250 ml reaction flask at 50° C. during 30 minutes. The pre-polymer was then transferred to a precipitate flask of 1000 ml and 14.88 grams of TDI (Toluene diisocyanate) were added, and stirred mechanically for 3 hours maintaining temperature at 70° C. Once the reaction was completed the pre-polymer was cooled to 50° C. and 4.96 grams of MEKO (Methyl ethyl ketoxima) were added to block the free NCO groups. This reaction took place during 2 hours. Finally, 2.88 grams of TEA (Triethylamine) were added during 30 minutes with vigorous agitation maintaining the temperature at 50° C. An amount of 50% w/w of water was then added drop by drop to form an emulsion.

Example 11—Preparation of a Polyurethane Varnish from Polyol Obtained by Route 1 of the Second Method The pre-polymer was formed taking 12 g of polyol, 50 g surfactant and 10 ml of MEK (methyl ethyl ketone) in a 250 ml reaction flask at 50° C. during 30 minutes. The pre-polymer was then transferred to a precipitate flask of 1000 ml and 12.52 grams of TDI (Toluene diisocyanate) were added, and stirred mechanically for 3 hours maintaining temperature at 70° C. Once the reaction was completed the pre-polymer was cooled to 50° C. and 5 grams of MEKO (methyl ethyl ketoxima) were added to block the free NCO groups. This reaction took place during 2 hours. Finally, 2.2 grams of TEA (Triethylamine) were added during 30 minutes with vigorous agitation maintaining the temperature at 50° C. An amount of 50% w/w of water was then added drop by drop to form an emulsion.

Example 12—Preparation of a Polyurethane Foam from Polyol Obtained by Route 2

13 g of palm polyol were taken and a mixture 50:50 performed with diethylene glycol, placed on a heating surface with magnetic agitation to 800 rpm, and then 0.04 g of surfactant, 0.02 g of DBTL (Dibutilin dilaurate) as catalyst and 0.2 g of water were added. Finally, 3.8 g of TDI (Toluene diisocyanate) were added and rapidly stirred manually. This reaction this is highly exothermic.

Example 13—Preparation of a Foam of Polyurethane to from of Polyol Obtained with the Route 3

10 g of palm polyol were taken and a mixture 50:50 performed with diethylene glycol, placed on a heating surface with magnetic agitation to 800 rpm, and then 0.27 g of surfactant, 0.19 g of DBTL (Dibutilin dilaurate) as catalyst and 2.69 g of water were added. Finally, 13.2 g of TDI (Toluene diisocyanate) were added and rapidly stirred manually. This reaction this is highly exothermic.

Example 14—Preparation of Polyurethane Foam from Polyol Obtained by Route 4

10 g of palm polyol and 10 g of DEG (diethylene glycol) were weighed, then 0, 19 g of DBTL (Dibutyltin dilaurate) catalyst were added, followed by 2.69 g of water and 0.27 g of surfactant. This premix was stirred at room temperature for a few minutes and then 13.24 g of MDI were added. This reaction is highly exothermic.

Example 15—Preparation of a Polyurethane Foam from Polyol Obtained from Example 6

9 grams of polyol and 1 gram of 1,6 butanediol were premixed and submitted to heating in case that the polyol was in a solid state. 0.15 grams of silicone 193C and 0.03 grams DBTL (Dibutyltin dilaurate) were then added and mixed for homogeneity; and finally 1.98 grams of TDI (Toluene diisocyanate) were added and stirred vigorously. The reaction this is highly exothermic.

Example 16—Preparation of Rigid Polyurethane from Polyol Obtained in Example 7

9 grams of polyol and 1 gram of SDR (Diethylene glycol) are mixed. The mixture, which is solid, is heated. 0.15 grams of silicone 193C and 0.03 grams of DBTL (Dibutyltin dilaurate) were added and mixed to achieve homogeneity, and finally 10.5 grams of polymeric MDI (Methylene diisocyanate) are added and stirred vigorously. The reaction is highly exothermic.

Example 17—Preparation of Rigid Polyurethane from Polyol Obtained in Example 8

9 grams of polyol and 1 gram of SDR (Diethylene glycol) are mixed. The mixture, which is solid, is heated. 0.15 grams of silicone 193C and 0.03 grams of DBTL (Dibutyltin dilaurate) were added and mixed to achieve homogeneity, and finally 10.5 grams of polymeric MDI (Methylene diisocyanate) are added and stirred vigorously. The reaction is highly exothermic.

Example 18—Preparation of Flexible Polyurethane from Polyol Obtained in Example 9

8.5 grams of polyol and 1.5 grams of butanediol are mixed. The mixture, which is solid, is heated. 0.15 grams of silicone 193C, 0.1 grams of water, and 0.03 grams of DBTL (Dibutyltin dilaurate) were added and mixed to achieve homogeneity, and finally 4.28 grams of polymeric TDI (toluene diisocyanate) are added and stirred vigorously. The reaction is highly exothermic.

A feature of polyols and of products obtained from these, in view of the previous examples, has yielded the following ranges of properties:

Polyols with molecular weights between 314 and 3366 and with a hydroxyl number between 50 and 450 mgKOH/g sample.

The rigid foams resulting were tested regarding density (according to ASTM C373-88) with results between 0.284 and 0.658 g/cm$^3$, Young module (according to ASTM 0695-10) with results between 8.94522 and 54.92330 MPa, and maximum effort (according to ASTM 0695-10) with results between 0.92037 and 8.29101 MPa.

The semi-rigid foams resulting were tested regarding density (according to ASTM C373-88) with results between 0.120 and 0.158 g/cm3, Young module (according to ASTM 0695-10) with results between 0.78727 and 1.54311 MPa, and maximum effort (according to ASTM 0695-10) with results between 0.07012 and 0.09753 MPa.

Example 19—Additional Experimental Runs

Initially we start from the 4 mother routes (Routes 1-4, considering that Route 1 comprises Methods I and II). From these routes other routes are derived in the order below:

| Mother Route | Derived Route |
|---|---|
| 1 | 1 |
|  | 5 |
|  | 9 |
|  | 13 |
|  | 17 |
|  | 21 |
|  | 25 |
| 2 | 2 |
|  | 6 |
|  | 10 |
|  | 14 |
|  | 18 |
|  | 22 |
|  | 26 |
| 3 | 3 |
|  | 7 |
|  | 11 |
|  | 15 |
|  | 19 |
|  | 23 |
|  | 27 |
| 4 | 4 |
|  | 8 |
|  | 12 |
|  | 16 |
|  | 20 |
|  | 24 |
|  | 28 |

In the following table the different experimental runs are summarized, defined by the following parameters:

Route Number

Polyol preparation: reagents operating conditions evaluation results

Preparation of polyurethane: reagents operating conditions product characteristics evaluation results The abbreviation "NA" indicates that the indicated procedure was not carried out, as it did not become of interest for the inventors.

| Route | Experiment No. | Preparation of polyol | | | Preparation of Polyurethane | | | |
|---|---|---|---|---|---|---|---|---|
| | | Reagents | Operational conditions | Evaluation Results | Reagents | Operational conditions | Product Features | Evaluation Results |
| 1-Method 1 | 1 | Palm Oil maleic anhydride | Maleinisation: T = 180° C.; nitrogen t = 3 h | 0.23 mgKOH/g sample | Prepolymer (polyol), MEKO, TEA, HDI | Isocyanate reaction: t = 3 h, T = 70° C. Blocking with MEKO: T = 50 C., t = 2 h. Neutralization with TEA: T = 50 C., t = 30 min, constant stirring. | The varnish is separated into two phases. Silicone varnish intermediately is observed, appears to be in excess. Dark brown initially, but eventually turns light brown. Opaque appearance. Appearance is that of a dispersion (bubbles are observed). | |
| 1-Method 2 | 1 | Palm Oil Maleic anhydride Glycerin (99.5% purity) Sodium Hydroxide Sodium Chloride Sulfuric acid (99.5% purity) Methyl ethyl ketone (MEK) Sulfonic Toluene Acid Toluene maleic anhydride TDI (toluene diisocyanate) Methyl ethyl ketoxime (MEKO, 99.5% purity). Ethanol | t = 30 min. 2 Rotoevaporation: T = 80° C., 800 rpm, vacuum conditions. 3. Blocking MEK: T = 90° c., t = 2 h. 4. Blocked monoglyceride: T = 90° C., t = 3.5 h, 200 rpm. 5. Rotoevaporation: T = 80° C., 800 rpm, vacuum conditions. 6. Maleinization: T = 200° C.; nitrogen t = 3 h. Rotoevaporation: T = 80° C., 800 rpm, vacuum condition, t = 1.5 h. | | Pre-polymer (polyol) HDI MEKO TEA | Isocyanate reaction: t = 3 h, T 70° C. Blocking with MEKO: T = 50 C., t = 2 h. Neutralization with TEA: T = 50 C., t = 30 min, constant stirring. | | |
| 1-Method 1 | 1 | Palm Oil Maleic anhydride | Maleinisation: T = 180° C.; nitrogen t = 3 h | | Prepolymer (polyol), MEKO, TEA, HDI | Isocyanate reaction: t = 3 h, T = 70° C. Blocking with MEKO: T = 50 C., t = 2 h. Neutralization with TEA: T = 50 C., t = 30 min, constant stirring. | It is a viscous mixture in which the silicone is completely separated. Color dark brown. It contains lots of granules. Freshly prepared separately is much | |

-continued

| Route | Experiment No. | Preparation of polyol | | | Preparation of Polyurethane | | |
| --- | --- | --- | --- | --- | --- | --- | --- |
| | | Reagents | Operational conditions | Evaluation Results | Reagents | Operational conditions | Product Features | Evaluation Results |
| 1-Method 1 | 2 | Palm Oil maleic anhydride | Maleinisation: T = 180° C.; nitrogen t = 3 h | 1.32 mgKOH/g sample | NA | NA | eventually improves the homogeneity of the mixture. | NA |
| 1-Method 1 | 3 | Palm Oil maleic anhydride | Maleinisation: T = 180° C.; nitrogen t = 3 h | 1.43 mgKOH/g sample | NA | NA | NA | NA |
| 1-Method 2 | 1 | Palm Oil maleic anhydride Glycerin (99.5% purity) Sodium Hydroxide Sodium Chloride Sulfuric acid (99.5% purity) Ethyl methyl ketone (MEK) Sulfonic Acid Toluene Toluene Maleic anhydride Toluene diisocyanate (TDI) Methyl ethyl Ketoxima (MEKO, 99.5% purity). Ethanol | Maleinisation: T = 180° C.; nitrogen t = 3 h | 2.41 mgKOH/g sample | Prepolymer (polyol), TDI MEKO TEA | Isocyanate reaction: t = 3 h, T = 70° C. Blocking with MEKO: T = 50 C., t = 2 h. Neutralization with TEA: T = 50 C, t = 30 min, constant stirring. | Smooth varnish. Beige Color. Medium viscosity. Strong odor. | |
| 1-Method 2 | 2 | Palm Oil Maleic anhydride Glycerin (99.5% purity) Sodium Hydroxide Sodium Chloride Sulfuric acid (99.5% purity) Methyl ethyl ketone (MEK) Sulfonic Toluene Acid Toluene maleic anhydride TDI (toluene diisocyanate) Methyl ethyl | Maleinisation: T = 180° C.; nitrogen t = 3 h | 27.13 mgKOH/g sample | NA | NA | NA | NA |

| Route | Experiment No. | Preparation of polyol | | | Preparation of Polyurethane | | | |
|---|---|---|---|---|---|---|---|---|
| | | Reagents | Operational conditions | Evaluation Results | Reagents | Operational conditions | Product Features | Evaluation Results |
| 1-Method 2 | 3 | Ketoxima (MEKO, 99.5% purity). Ethanol Palm Oil Maleic anhydride Glycerin (99.5% purity) Sodium Hydroxide Sodium Chloride Sulfuric acid (99.5% purity) Methyl ethyl ketone (MEK) Sulfonic Toluene Acid Toluene maleic anhydride TDI (toluene diisocyanate) Methyl ethyl Ketoxima (MEKO, 99.5% purity). Ethanol | Maleinisation: T = 180° C.; nitrogen t = 3 h | 15.03 mgKOH/g sample | NA | NA | NA | |
| 6 | 1 | Palm Oil Glycerol Sodium Hydroxide Terbutanol. (20 ml) Hydrochloric Acid n-Hexane. (40 ml) | Glycerolysis: T = 90° C., t = 2 h. Roto-evaporation at low temperature, according to the volatility of hexane. | 19.33 mgKOH/g sample | Diethylene TDI Surfactant Dibutyltin Dilaurate (DBTDL). water | T, P atmospheric, vigorous manual shaking | Yellow. Solid appearance, it appears greasy. Not observed porous | |
| 6 | 2 | Palm Oil Glycerol Sodium hydroxide Terbutanol. (20 ml) Hydrochloric Acid n-Hexane. (40 ml) | Glycerolysis: T = 90° C., t = 2 h. Roto-evaporation at low temperature, according to the volatility of hexane. | | polyethylene glycol TDI Surfactant Dibutyltin Dilaurate (DBTDL) water | T, P atmospheric, vigorous manual shaking | Ddid not form a foam. When reacting remained gritty and when put in the soft mold it becomes soft to the touch, with time it hardened. Its color is pale yellow. | |
| 20 | 1 | Palm oil methanol Sodium Hydroxide Phosphoric acid (H3PO4) Hydrogen Peroxide (H2O2) benzene | Methanolysis: Temperature: 70° C., t = 1.5 h, agitation: 1000 rpm. Rotoevaporation: T = 80° C., t = 3 h, vacuum conditions. Epoxidation: T = 40° C., | | Palm Polyol diethylene glycol surfactant catalyst water IPDI | T, P atmospheric, vigorous manual shaking | Porous foam. Initially its color was white, but was oxidized and a clear yellow was taken. It is solid but appears liquid on the surface, seems | |

-continued

| Route | Experiment No. | Preparation of polyol | | | Preparation of Polyurethane | | | Evaluation Results |
|---|---|---|---|---|---|---|---|---|
| | | Reagents | Operational conditions | Evaluation Results | Reagents | Operational conditions | Product Features | |
| 20 | | diethylene glycol (DEG) Formic acid Sodium Chloride | agitation 800 rpm, t = 3 h. Rotoevaporation: T = 90° C., t = 4 h. | | | | excess reagent, possibly is isocyanate. Feels stiff to the touch. | |
| | 2 | Palm oil Methanol Sodium Hydroxide Phosphoric acid (H3P04) Hydrogen peroxide (H2O2) benzene Diethylene glycol (DEG). formic acid Sodium Chloride | Methanolysis: Temperature: 70° C., t = 1.5 h, agitation: 1000 rpm. Rotoevaporation: T = 80° C., t = 3 h, vacuum conditions. Epoxidation: T = 40° C. Agitation: 800 rpm, t = 3 h. Rotoevaporation: T = 90° C., t = 4 h. | Palm Polyol | T, P atmospheric surfactant catalyst water IPDI | vigorous manual shaking. | It is a color foam. White pores was observed. Wet, it appears a bit greasy. It is a consistent solid. | |
| 2 | 1 | Palm oil. Glycerol Sodium Hydroxide Terbutanol. (20 ml) Hydrochloric Acid. n-Hexane. (40 ml) | Glycerolysis: T = 90° C. t = 2 h. Roto-evaporation at low temperature, according to the volatility of hexane. | | diethylene glycol HDI Surfactant Dilaurate dibutyltin (DBTDL) water | T, P atmospheric, vigorous manual shaking. | Orange. Homogeneous. Played more rigid than others. Initially it looks like a slurry. It takes a little time to become solid. | |
| 2 | 2 | Palm oil Glycerol Sodium Hydroxide Terbutanol. (20 ml) Hydrochloric Acid. n-Hexane. (40 ml) | Glycerolysis: T = 90° C., t = 2 h. Roto-evaporation at low temperature, according to the volatility of hexane. | | Polyethyllenneglycol HDI Surfactant Dilaurate dibutyltin (DBTDL) water | T, P atmospheric, vigorous manual shaking. | The mixture is sandy. Dark yellow. No foam was formed. | |
| 2 | 3 | Palm oil. Glycerol sodium hydroxide Terbutanol. (20 ml) Hydrochloric Acid. n-Hexane. (40 ml) | Glycerolysis: T = 90° C., t = 2 h. Roto-evaporation at low temperature, according to the volatility of hexane. | | polyethylene glycol HDI Surfactant Dilaurate dibutyltin (DBTDL) water | T, P atmospheric, vigorous manual shaking | It was prepared using an index of 0.5. It is a weak consistency polymer, orange, it breaks easily. Over time white pieces presented themselves. | |
| 2 | 4 | Palm oil. Glycerol Sodium Hydroxide Tert-butanol (20 ml) Hydrochloric Acid. | Glycerolysis: T = 90° C., t = 2 h. Roto-evaporation at low temperature, according to the volatility of hexane | 23.13 mgKOH/g sample | polyethylene glycol HDI Surfactant Dilaurate dibutyltin (DBTDL) water | T, P atmospheric, vigorous manual shaking | It was prepared using an index of 0.8. It is a product a little harder than the 0.5 index, however it is | |

| Route | Experiment No. | Preparation of polyol | | | Preparation of Polyurethane | | | |
|---|---|---|---|---|---|---|---|---|
| | | Reagents | Operational conditions | Evaluation Results | Reagents | Operational conditions | Product Features | Evaluation Results |
| 2 | 5 | Palm oil Glycerol Sodium Hydroxide Terbutanol. (20 ml) Hydrochloric Acid. n-Hexano. (40 ml) | Glycerolysis: T = 90° C., t = 2 h. Roto-evaporation at low temperature, according to the volatility of hexane | | polyethylene glycol HDI Surfactant Dilaurate dibutyltin (DBTDL) water | T, P atmospheric, vigorous manual shaking | still very fragile. Orange It was developed with an index of 1. Orange, it is a product a little stronger than the 0.8 index, however it is even more fragile than expected. | |
| 2 | 6 | Palm oil. Glycerol. Sodium Hydroxide Tert-butanol (20 ml) Hydrochloric Acid. n-Hexane. (40 ml) | Glycerolysis: T = 90° C., t = 2 h. Roto-evaporation at low temperature, according to the volatility of hexane | | Polyethyleneglycol HDI Surfactant Dilaurate dibutyltin (DBTDL) water | T, P atmospheric, vigorous manual shaking | Made with an index of 12. Orange product, stronger that lower indices, as it consistency is harder; however, it is still brittle and does not exhibit the desired rigidity | |
| 2 | 7 | Palm oil Glycerol. | Glycerolysis: T = 90° C., t = 2 h. Roto-evaporation at low temperature, according to the volatility of hexane | 523.23 mgKOH/g sample | NA | NA | NA | NA |
| 2 | 8 | Palm oil. Glycerol. Lead Oxide Tert-butanol (20 ml) Hydrochloric Acid. n-Hexane. (40 ml) | Glycerolysis: T = 215° C., t = 1 h. Agitation = 1000 rpm. Roto-evaporation at 60°, t = 5 h. | | | | | |
| 4 | 1 | Palm oil Methanol Sodium Hydroxide Phosphoric acid (H3PO4) Hydrogen Peroxide (H2O2) Benzene Formic Acid Sodium Chloride | Methanolysis: T: 70° C.m t = 2.5 h. Agitation 1000 rpm. Rotoevaporation: T = 80° C., t = 3 h, vacuum conditions. Epoxidation: T = 40° C.: Agitation: 800 rpm, t = 3 h. Rotoevaporation: T = 90° C., t = 4 h. | | Palm Polyol diethylene glycol Surfactant Catalyst Water HDI | T, P atmospheric, vigorous manual shaking | White color solid with good homogeneity. Observed as somewhat greasy. Liquid on the surface. | |
| 4 | 2 | Palm oil. Methanol Sodium Hydroxide Phosphoric Acid (H3PO4) Hydrogen Peroxide (H2O2) | Methanolysis: T: 70° C., t = 1.5 h. Agitation 1000 rpm. Rotoevaporation: T = 80° C., t = 3 h, vacuum conditions. | | Palm Polyol Diethylene glycol Surfactant Catalyst Water | T, P atmospheric, vigorous manual shaking | Clear yellow color. The mixture exhibited good homogeneity. Consistent solid. Creamy to the touch. | |

| Route | Experiment No. | Reagents | Preparation of polyol Operational conditions | Evaluation Results | Preparation of Polyurethane Reagents | Operational conditions | Product Features | Evaluation Results |
|---|---|---|---|---|---|---|---|---|
| | | Benzene Diethylene glycol (DEG). Formic Acid Sodium Chloride | Epoxidation: T = 40° C., Agitation 800 rpm, t = 3 h. Rotoevaporation: T = 90° C., t = 4 h. | | HDI | | | |
| 4 | 3 | Palm Oil Methanol Sodium Hydroxide Phosphoric Acid (H3PO4) Hydrogen Peroxide (H2O2) Benzene Diethylene glycol (DEG). Formic Acid Sodium Chloride | Methanolysis: T: 70° C., t = 1.5 h. Agitation 1000 rpm. Rotoevaporation: T = 80° C., t = 3 h., vacuum conditions. Epoxidation: T = 40° C., Agitation 800 rpm, t = 3 h. Rotoevaporation: T = 90° C., t = 4 h. | 2.21 mgKOH/g sample | NA | NA | NA | |
| 4 | 4 | Palm Oil Methanol Sodium Hydroxide Phosphoric Acid (H3PO4) Hydrogen Peroxide (H2O2) Benzene Diethylene glycol (DEG). Formic Acid Sodium Chloride | Methanolysis: T: 70° C., t = 1.5 h. Agitation 1000 rpm. Rotoevaporation: T = 80° C., t = 3 h., vacuum conditions. Epoxidation: T = 40° C., Agitation 800 rpm, t = 3 h. Rotoevaporation: T = 90° C., t = 4 h. | | NA | NA | NA | |
| 3 | 1 | Palm Oil PbO Pentaerythritol Tert-butanol (20 ml) Hydrochloric Acid. n-Hexane. (40 ml) | Reaction with pentaerythritol: T = 200° C., inert atmosphere, t = 2 h. | | | T, P atmospheric, vigorous manual shaking | Polymer with a grasslike and brittle consistency. Cream colored. Allows mold flow. | |
| 3 | 2 | Palm oil PbO Pentaerythritol Tert-butanol (20 ml) Hydrochloric Acid. n-Hexane. (40 ml) | Reaction with pentaerythritol: T = 200° C., inert atmosphere, t = 2 h. | 11.86 mgKOH/g sample | NA | NA | NA | |
| 3 | 3 | Palm oil PbO Pentaerythritol Tert-butanol (20 ml) Hydrochloric Acid. n-Hexane. (40 ml) | Reaction with pentaerythritol: T = 200° C., inert atmosphere, t = 2 h. | | NA | NA | NA | |

-continued

| Route | Experiment No. | Preparation of polyol | | Evaluation Results | Preparation of Polyurethane | | | Evaluation Results |
|---|---|---|---|---|---|---|---|---|
| | | Reagents | Operational conditions | | Reagents | Operational conditions | Product Features | |
| 5-Method 1 | 1 | Palm oil Maleic Anhydride | Maleinisation: T0 180° C.; Nitrogen atmosphere, t = 3 h. | | Pre-polymer MeKO, HDI, TEA | Reaction with isocyanate: t = 3 hr, T = 70° C. MEKO Blockage: T = 50° C., t = 2 hr. Neutralization with TEA: T = 50° C., t = 30 min., constant agitation. | This product did not yield varnish, as it became a solid. | |
| 5-Method 2 | 1 | Palm oil Maleic Anhydride Glycerin (99.5% purity) Sodium Hydroxide Sodium Chloride Sulfuric Acid (99.5% purity) Methyl ethyl ketone (MEK) Sulfonic Toluene Acid Toluene Maleic Anhydride Toluene disiocyanate (TDI) Methyl ethyl Ketoxima (MEKO, 99.5% purity). Ethanol | Maleinisation: T = 180° C.; Nitrogen atmosphere, t = 3 h. | | Pre-polymer (polyol) MDI Meko TEA | Reaction with isocyanate: t = 3 hr, T = 70° C. MEKO Blockage: T = 50° C., t = 2 hr. Neutralization with TEA: T = 50° C., t = 30 min., constant agitation. | This varnish exhibits phase separation. | |
| 7 | 1 | Palm Oil PbO Pentaerythritol Tert-butanol (20 ml) Hydrochloric Acid. n-Hexane. (40 ml) | Reaction with pentaerythritol: T = 200° C., inert atmosphere, t = 2 h. | | Palm Polyol Diethylene glycol Surfactant Catalyst Water HDI | T, P atmospheric, vigorous manual shaking | Foam with a greasy aspect. Very sticky. Yellow color. Difficult to remove as a whole. | |
| 7 | 2 | Palm oil PbO Pentaerythritol Tert-butanol (20 ml) Hydrochloric Acid. n-Hexane. (40 ml) | Reaction with pentaerythritol: T = 200° C., inert atmosphere, t = 2 h. | | Palm Polyol Surfactant Catalyst Water TDI | T, P atmospheric, vigorous manual shaking | This product is a modification of the route initially planned, because the Polyol used iso nly palm oil polyol. Its consistency is a very brittle foam. Clear yellow color. Does not appear greasy and dries more rapidly thatn the product of this route where the | |

-continued

| Route | Experiment No. | Preparation of polyol | | | Preparation of Polyurethane | | |
|---|---|---|---|---|---|---|---|
| | | Reagents | Operational conditions | Evaluation Results | Reagents | Operational conditions | Product Features | Evaluation Results |
| 8 | 1 | Palm oil, methanol, Sodium Hydroxide, Phosphoric acid (H3PO4), Hydrogen Peroxide (H2O2), benzene, diethylene glycol (DEG), Formic acid, Sodium Chloride | Methanolysis: T: 70° C., t = 1.5 h. Agitation 1000 rpm. Rotoevaporation: T = 80° C., t = 3 h., vacuum conditions. Epoxidation: T = 40° C., Agitation 800 rpm, t = 3 h. Rotoevaporation: T) 90° C., t = 4 h. | | Palm Polyol, Diethylene glycol, Surfactant, Catalyst, Water, MDI | T, P atmospheric, vigorous manual shaking | polyol Combined with the DEG. A white foam, appears somewhat porous. Consistent, but appears brittle. | |
| 78 | 2 | Palm oil, methanol, Sodium Hydroxide, Phosphoric acid (H3PO4), Hydrogen Peroxide (H2O2), benzene, diethylene glycol (DEG), Formic acid, Sodium Chloride | Methanolysis: T: 70° C., t = 1.5 h. Agitation 1000 rpm. Rotoevaporation: T = 80° C., t = 3 h., vacuum conditions. Epoxidation: T = 40° C., Agitation 800 rpm, t = 3 h. Rotoevaporation: T) 90° C., t = 4 h. | | Palm Polyol, Surfactant, Catalyst, Water, TDI | T, P atmospheric, vigorous manual shaking | White color foam. Its appearance is similar to gypsum. Very brittle. | |
| 9 | 1 | Palm oil, Maleic Anhydride | Methanolysis: T: 180° C., Nitrogen atmosphere, t = 3 hr. | | Pre-polymer (polyol), MEKO, TEA, TDI | Reaction with isocyanate: t = 3 hr, T = 70° C. MEKO Blockage: T = 50° C., t = 2 hr. Neutralization with TEA: T = 50° C., t = 30 min., constant agitation. | Coffee-colored varnish. Easily separated as it does not have low stability, when left in repose two phases are observed and a semisolid layer at the bottom. Pores observed in its interior. | |
| 9-Method 2 | 1 | Palm Oil, Maleic anhydride (99.5% purity), Glycerin (99.5% purity), Sodium Hydroxide, Sodium Chloride, Sulfuric acid (99.5% purity), Methyl ethyl ketone (MEK) | Methanolysis: T: 180° C., Nitrogen atmosphere, t = 3 hr. | | Prepolymer (polyol), TDI, Meko, TEA | Reaction with isocyanate: t = 3 hr, T = 70° C. MEKO Blockage: T = 50° C., t = 2 hr. Neutralization with TEA: T = 50° C., t = 30 min, constant agitation. | This product did not yield a varnish, as it solidified. Coffee colored solid paste. | |

| Route | Experiment No. | Preparation of polyol | | Preparation of Polyurethane | | | Evaluation Results |
|---|---|---|---|---|---|---|---|
| | | Reagents | Operational conditions | Evaluation Results | Reagents | Operational conditions | Product Features |
| | | Sulfonic Toluene Acid Toluene maleic anhydrite TDI (toluene diisocyanate) Methyl ethyl Ketoxima (MEKO, 99.5% purity). Ethanol. | | | | | |
| 5 | 1. Polyol of crude palm oil using PbO | Palm Oil Hydrogen Peroxide Formic acid Sodium Bicarbonate Sodium Chloride Glycerin Lead Oxide | Epoxidation: Temperature = 50° C. Time: 4 hrs. Agitation: 800 rpm Glycerolysis Temp = 215° C. Time = 45 mins. Agitation: 1300 rpm | # OH = 105.52 mg KOH/g sample | Palm polyol Diethylene glycol Dibutyltin Dilaureate (DBTDL) Silicone 193C Toluene isocyanate (TDI) | Vigorous agitation Ambient temperature | Rapid growth of the foam which solidified immediately. Rigid foam is not greasy to the touch. |
| 6 | 1. Polyol of crude palm oil using PbO | Crude palm oil Hydrogen Peroxide Formic acid Sodium Bicarbonate Sodium Chloride Glycerin Sodium Hydroxide Phosphoric Acid | Epoxidation: Temperature = 50° C. Time: 4 hrs. Agitation: 800 rpm Glycerolysis Temp = 215° C. Time = 45 mins. Agitation: 1300 rpm | # OH = 202.43 mg KOH/g sample | | | Reaction with continuous bubbling and release of heat, after a half hour product has not solidified, an excess of isocyanate is observed. |
| 7 | 1. Oil Polyol Of RBD NaOH palm. | RBD Palm Oil Hydrogen Peroxide Formic acid Sodium Bicarbonate Sodium Chloride Glycerin Sodium Hydroxide Phosphoric Acid | Epoxidation: Temperature = 50° C. Time: 4 hrs. Agitation: 800 rpm Glycerolysis Temp = 215° C. Time = 45 mins. Agitation: 1300 rpm | # OH = 418.83 mg KOH/g sample | Palm Polyol Diethylene glycol Dibutyltin Dilauate (DBTDL) Silicon 193C Methylene diisocyanate (MDI) | Vigorous agitation Ambient temperature | Semi-rigid polyurethane, color Yellowish, solidified rapidly. |
| 8 | 1. Polyol of palm oil RBD PbO | RBD Palm Oil Hydrogen Peroxide Formic acid Sodium Bicarbonate Sodium Chloride Glycerin | Epoxidation: Temperature = 50° C. Time: 4 hrs. Agitation: 800 rpm Glycerolysis Temp = 215° C. | # OH = 81.59 mg KOH/g sample | Palm polyol Diethylene glycol Dibutyltin Dilauate (DBTDL) Silicon 193C Toluene isocyanate (TDI) | Vigorous agitation Ambient temperature | The product has a grasslike consistence and there was no evience of reaction, such as release of heat. |

| Route | Experiment No. | Preparation of polyol | | | Preparation of Polyurethane | | | Evaluation Results |
|---|---|---|---|---|---|---|---|---|
| | | Reagents | Operational conditions | Evaluation Results | Reagents | Operational conditions | Product Features | |
| Combined 2 and 4 | 1 | Lead Oxide Olein Phase of palm oil Hydrogen Peroxide Formic acid Sodium Bicarbonate Sodium Chloride Glycerin Lead Oxide | Time = 45 mins. Agitation: 1300 rpm Epoxidation: Temperature = 50° C. Time: 4 hrs. Agitation: 800 rpm Glycerolysis Temp = 215° C. Time = 45 mins. Agitation: 1300 rpm | # OH = 105.52 mg KOH/g sample | Palm polyol Diethylene glycol Dibutyltin Dilauate (DBTDL) Silicone 193C Toluene isocyanate (TDI) | Vigorous agitation Ambient temperature | The mixture begins to rise instantly forming a low density foam, it Evidence of a very large pore size and low consistency. This product does not allow flow, nor removal from the mold. | |
| | 2 | Olein Phase of palm oil Hydrogen Peroxide Formic acid Sodium Bicarbonate Sodium Chloride Glycerin Sodium Hydroxide Phosphoric Acid | Epoxidation: Temperature = 50° C. Time: 4 hrs. Agitation: 800 rpm Glycerolysis Temp = 215° C. Time = 45 mins. Agitation: 1300 rpm | # OH = 202.43 mg KOH/g sample | Palm Polyol Dibutyltin Dilauate (DBTDL) Silicon 193C Methylene diisocyanate (MDI) Water | Vigorous agitation Ambient temperature | No evidence of reaction, a viscous yellow liquid pours when emptying the mold. After 1 day it still has not solidified. | |
| | 3 | Olein Phase of palm oil Hydrogen Peroxide Formic acid Sodium Bicarbonate Sodium Chloride Glycerin Sodium Hydroxide Phosphoric Acid | Epoxidation: Temperature = 50° C. Time: 4 hrs. Agitation: 800 rpm Glycerolysis Temp = 215° C. Time = 45 mins. Agitation: 1300 rpm | # OH = 418.83 mg KOH/g sample | Palm Polyol Water Dibutyltin Dilauate (DBTDL) Silicon 193C Methylene diisocyanate (MDI) | Vigorous agitation Ambient temperature | Brittle foam that grows rapidly and whose interior is not compact. | |
| | 4 | Olein Phase of palm oil Hydrogen Peroxide Formic acid Sodium Bicarbonate Sodium Chloride Glycerin | Epoxidation: Temperature = 50° C. Time: 4 hrs. Agitation: 800 rpm Glycerolysis Temp = 215° C. | # OH = 105.52 mg KOH/g sample | Palm Polyol Water Dibutyltin Dilauate (DBTDL) Silicon 193C Methylene diisocyanate (MDI) | Vigorous agitation Ambient temperature | No evidence of reaction, emptying of the mold yields a viscous yellowish creamy liquid. | |

-continued

| Route | Experiment No. | Preparation of polyol | | | Preparation of Polyurethane | | | |
|---|---|---|---|---|---|---|---|---|
| | | Reagents | Operational conditions | Evaluation Results | Reagents | Operational conditions | Product Features | Evaluation Results |
| | | Lead oxide | Time = 45 mins. Agitation: 1300 rpm | | | | | |
| | 5 | Olein Phase of palm oil | Epoxidation: | # OH = 81.59 mg KOH/g sample | Palm Polyol | Vigorous agitation | A very compact product was obtained but it is very fragile to contact. | |
| | | Hydrogen Peroxide | Temperature = 50° C. | | Water | Ambient temperature | | |
| | | Formic acid | Time = 4 hrs. | | Dibutyltin Dilauate (DBTDL) | | | |
| | | Sodium Bicarbonate Sodium Chloride | Agitation: 800 rpm Glycerolysis | | Silicon 193C Toluene isocyanate (TDI) | | | |
| | | Glycerin Lead oxide | Temp = 215° C. Time = 45 mins. Agitation: 1300 rpm | | | | | |
| | 6 | Olein Phase of palm oil | Epoxidation: | # OH = 202.43 mg KOH/g sample | Palm Polyol | Vigorous agitation | Material is rigid to the touch, dries quickly, not greasy, pores are smaller than for foams obtained before, medium density. An excess of isocyanate is observed. | |
| | | Hydrogen Peroxide | Temperature = 50° C. | | Diethylene glycol | Ambient temperature | | |
| | | Formic acid | Time = 4 hrs. | | Dibutyltin Dilauate (DBTDL) | | | |
| | | Sodium Bicarbonate Sodium Chloride | Agitation: 800 rpm Glycerolysis | | Silicon 193C Methylene diisocyanate (MDI) | | | |
| | | Glycerin Sodium Hydroxide Phosphoric acid | Temp = 215° C. Time = 45 mins. Agitation: 1300 rpm | | | | | |
| | 7 | Olein Phase of palm oil | Epoxidation: | # OH = 418.83 mg KOH/g sample | Palm Polyol | Vigorous agitation | Rigid foam, higher density and smaller pore size than the prior one. Color is beige, with a tendency to light yellow. | |
| | | Hydrogen Peroxide | Temperature = 50° C. | | Diethylene glycol | Ambient temperature | | |
| | | Formic acid | Time = 4 hrs. | | Dibutyltin Dilauate (DBTDL) | | | |
| | | Sodium Bicarbonate Sodium Chloride | Agitation: 800 rpm Glycerolysis | | Silicon 193C Toluene isocyanate (TDI) | | | |
| | | Glycerin Sodium Hydroxide Phosphoric acid | Temp = 215° C. Time = 45 mins. Agitation: 1300 rpm | | | | | |
| | 8 | Olein Phase of palm oil | Epoxidation: | # OH = 105.52 mg KOH/g sample | Palm Polyol | Vigorous agitation | Rigid foam, of greater density and lesser pore size than the prior one. Color is beige, with tendency to clear yellow. | |
| | | Hydrogen Peroxide | Temperature = 50° C. | | Diethylene glycol | Ambient temperature | | |
| | | Formic acid | Time = 4 hrs. | | Dibutyltin Dilauate (DBTDL) | | | |
| | | Sodium Bicarbonate Sodium Chloride | Agitation: 800 rpm Glycerolysis | | Silicon 193C Methylene diisocyanate (MDI) | | | |
| | | Glycerin | Temp = 215° C. | | | | | |

-continued

| Route | Experiment No. | Preparation of polyol | | | Preparation of Polyurethane | | |
|---|---|---|---|---|---|---|---|
| | | Reagents | Operational conditions | Evaluation Results | Reagents | Operational conditions | Product Features | Evaluation Results |
| | | Lead oxide | Time = 45 mins. Agitation: 1300 rpm | | | | | |
| | 9 | Olein Phase of palm oil | Epoxidation: | # OH = 81.59 mg KOH/g sample | Palm Polyol | Vigorous agitation | Rigid foam, medium density and smaller pore size than the prior one. Color is beige, with tendency to clear yellow. | |
| | | Hydrogen Peroxide | Temperature = 50° C. | | Diethylene glycol | Ambient temperature | | |
| | | Formic acid | Time: 4 hrs. | | Dibutyltin Dilauate (DBTDL) | | | |
| | | Sodium Bicarbonate Sodium Chloride | Agitation: 800 rpm Glycerolysis | | Silicon 193C Toluene isocyanate (TDI) | | | |
| | | Glycerin Lead oxide | Temp = 215° C. Time = 45 mins. Agitation: 1300 rpm | | | | | |
| | 10 | Olein Phase of palm oil | Epoxidation: | # OH = 202.43 mg KOH/g sample | Palm Polyol | Vigorous agitation | Rigid sandy polyurethane, good appearance. | |
| | | Hydrogen Peroxide | Temperature = 50° C. | | 1,6 butanediol (BDO) | Ambient temperature | | |
| | | Formic acid | Time: 4 hrs. | | Dibutyltin Dilauate (DBTDL) | | | |
| | | Sodium Bicarbonate Sodium Chloride | Agitation: 800 rpm Glycerolysis | | Silicon 193C Methylene diisocyanate (MDI) | | | |
| | | Glycerin Sodium Hydroxide Phosphoric acid | Temp = 215° C. Time = 45 mins. Agitation: 1300 rpm | | | | | |
| | 11 | Olein Phase of palm oil | Epoxidation: | # OH = 418.83 mg KOH/g sample | Palm Polyol | Vigorous agitation | A rigid white polyurethane was obtained, very hard. Does not permit agitation because the reaction is very fast. | |
| | | Hydrogen Peroxide | Temperature = 50° C. | | 1,6 butanediol (BDO) | Ambient temperature | | |
| | | Formic acid | Time: 4 hrs. | | Dibutyltin Dilauate (DBTDL) | | | |
| | | Sodium Bicarbonate Sodium Chloride | Agitation: 800 rpm Glycerolysis | | Silicon 193C Methylene diisocyanate (MDI) | | | |
| | | Glycerin Sodium Hydroxide Phosphoric acid | Temp = 215° C. Time = 45 mins. Agitation: 1300 rpm | | | | | |
| | 12 | Olein Phase of palm oil | Epoxidation: | # OH = 202.43 mg KOH/g sample | Palm Polyol | Vigorous agitation | Beige colored polymer, which exhibited good consistency. | |
| | | Hydrogen Peroxide | Temperature = 50° C. | | 1,6 butanediol (BDO) | Ambient temperature | | |
| | | Formic acid | Time: 4 hrs. | | Dibutyltin Dilauate (DBTDL) | | | |
| | | Sodium Bicarbonate Sodium Chloride | Agitation: 800 rpm Glycerolysis | | Silicon 193C Methylene diisocyanate (MDI) | | | |
| | | Glycerin | Temp = 215° C. | | | | | |

-continued

| Route | Experiment No. | Preparation of polyol | | | Preparation of Polyurethane | | | Evaluation Results |
|---|---|---|---|---|---|---|---|---|
| | | Reagents | Operational conditions | Evaluation Results | Reagents | Operational conditions | Product Features | |
| | 13 | Sodium Hydroxide Phosphoric acid Olein Phase of palm oil Hydrogen Peroxide Formic acid Sodium Bicarbonate Sodium Chloride | Time = 45 mins. Agitation: 1300 rpm Epoxidation: Temperature = 50° C. Time = 4 hrs. Agitation: 800 rpm Glycerolysis | # OH = 418.83 mg KOH/g sample | Palm Polyol 1,6 butanediol (BDO) Dibutyltin Dilauate (DBTDL) Silicon 193C Methylene diisocyanate (MDI) | Vigorous agitation Ambient temperature | A white high density foam was obtained, with oval pores, of rigid consistence. | |
| | 14 | Glycerin Sodium Hydroxide Phosphoric acid Olein Phase of palm oil Hydrogen Peroxide Formic acid Sodium Bicarbonate Sodium Chloride | Temp = 215° C. Time = 45 mins. Agitation: 1300 rpm Epoxidation: Temperature = 50° C. Time = 4 hrs. Agitation: 800 rpm Glycerolysis | # OH = 32.84 mg KOH/g sample | Palm Polyol Diethylene glycol Dibutyltin Dilauate (DBTDL) Silicone emulsion Methylene diisocyanate (MDI) | Vigorous agitation Ambient temperature | Manually agitated, however no typical features of rection were evidenced (temperature changes, bubbling, and growth of foam), on the contrary, the liquid aspect stayed. | |
| | 15 | Glycerin Sodium Hydroxide Phosphoric acid Olein Phase of palm oil Hydrogen Peroxide Formic acid Sodium Bicarbonate Sodium Chloride | Temp = 215° C. Time = 45 mins. Agitation: 1300 rpm Epoxidation: Temperature = 50° C. Time = 4 hrs. Agitation: 800 rpm Glycerolysis | # OH = 88.97 mg KOH/g sample | Palm Polyol 1,6 butanediol (BDO) Dibutyltin Dilauate (DBTDL) Silicone 193C Toluene isocyanate (TDI) Ethylenediamine Water | Vigorous agitation Ambient temperature | No formation of foam was witnessed. | |
| | 16 | Glycerin Sodium Hydroxide Phosphoric acid Olein Phase of palm oil Hydrogen Peroxide Formic acid Sodium Bicarbonate Sodium Chloride | Temp = 215° C. Time = 45 mins. Agitation: 1300 rpm Epoxidation: Temperature = 50° C. Time = 4 hrs. Agitation: 800 rpm Glycerolysis | # OH = 88.97 mg KOH/g sample | Palm Polyol 1,6 butanediol (BDO) Dibutyltin Dilauate (DBTDL) Silicone 193C Toluene isocyanate (TDI) | Vigorous agitation Ambient temperature | Bubbling was observed, as well as an increase in temperature and the foam that was seen solidifying completely. | |

-continued

| Route | Experiment No. | Preparation of polyol | | | Preparation of Polyurethane | | | |
|---|---|---|---|---|---|---|---|---|
| | | Reagents | Operational conditions | Evaluation Results | Reagents | Operational conditions | Product Features | Evaluation Results |
| | 17 | Glycerin<br>Sodium Hydroxide<br>Phosphoric Acid<br>Olein Phase of palm oil<br>Hydrogen Peroxide<br>Formic acid<br>Sodium Bicarbonate<br>Sodium Chloride | Temp = 215° C.<br>Time = 45 mins.<br>Agitation: 1300 rpm<br>Epoxidation:<br>Temperature = 50° C.<br>Time: 3 hrs.<br>Agitation: 950 rpm<br>Glycerolysis | # OH = 401.4 mg KOH/g sample | Ethylenediamine<br>Water<br>Palm polyol<br>Diethylene glycol<br>Dibutyltin Dilaureate (DBTDL)<br>Silicone emulsion<br>Methylene diisocyanate (MDI) | Vigorous agitiation<br>Ambient temperature | Rigid polyurethane with good consistency although the pore size is big. | |
| | 18 | Glycerin<br>Sodium Hydroxide<br>Phosphoric Acid<br>Olein Phase of palm oil<br>Hydrogen Peroxide<br>Formic acid<br>Sodium Bicarnonate<br>Sodium Chloride | Temp = 215° C.<br>Time = 45 mins.<br>Agitation: 1300 rpm<br>Epoxidation:<br>Temperature = 50° C.<br>Time: 3 hrs.<br>Agitation: 950 rpm<br>Glycerolysis | # OH = 401.4 mg KOH/g sample | Palm polyol<br>Diethylene glycol<br>Dibutyltin Dilaureate (DBTDL)<br>Silicone emulsion<br>Methylene diisocyanate (MDI) | Vigorous agitiation<br>Ambient temperature | Polymer with a small sized pore and good rigidity properties. | |
| | 19 | Glycerin<br>Sodium Hydroxide<br>Phosphoric Acid<br>Olein Phase of palm oil<br>Hydrogen Peroxide<br>Formic acid<br>Sodium Bicarnonate<br>Sodium Chloride | Temp = 215° C.<br>Time = 45 mins.<br>Agitation: 1300 rpm<br>Epoxidation:<br>Temperature = 50° C.<br>Time: 3 hrs.<br>Agitation: 950 rpm<br>Glycerolysis | # OH = 437.56 mg KOH/g sample | Palm Polyol<br>Diethylene glycol<br>Dibutyltin Dilaureate (DBTDL) | Vigorous agitiation<br>Ambient temperature | Polymer with a small pore size and Good properties for rigidity. Chosen for the characterizing range for rigid PU | Young module = 33.3293 Mpa<br>Maximum effort = 3.1673 Mpa |
| | 20 | Glycerin<br>Sodium Hydroxide<br>Phosphoric Acid<br>Olein Phase of palm oil<br>Hydrogen Peroxide<br>Formic acid<br>Sodium Bicarnonate<br>Sodium Chloride<br>Glycerin<br>Sodium Hydroxide<br>Phosphoric Acid | Temp = 215° C.<br>Time = 45 mins.<br>Agitation: 1300 rpm<br>Epoxidation:<br>Temperature = 50° C.<br>Time: 3 hrs.<br>Agitation: 950 rpm<br>Glycerolysis<br>Temp = 215° C.<br>Time = 45 mins.<br>Agitation: 1300 rpm | # OH = 433.08 mg KOH/g sample | Palm polyol<br>Diethylene glycol<br>Dibutyltin Dilaureate (DBTDL)<br>Silicone 193C<br>Methylene diisocyanate (MDI) | Vigorous agitiation<br>Ambient temperature | Presents homogeneity, good pore size, shows good rigidity. | |

| Route | Experiment No. | Preparation of polyol | | | Preparation of Polyurethane | | | Evaluation Results |
|---|---|---|---|---|---|---|---|---|
| | | Reagents | Operational conditions | Evaluation Results | Reagents | Operational conditions | Product Features | |
| | 21 | Olein Phase of palm oil<br>Hydrogen Peroxide<br>Formic acid | Epoxidation<br>Temperature = 50° C.<br>Time: 3 hrs. | # OH = 263.4 mg KOH/g sample | Palm Polyol<br>Diethylene glycol<br>Dibutyltin Dilaureate (DBTDL)<br>Silicone 193C<br>Methylene diisocyanate (MDI) | Vigorous agitation<br>Ambient temperature | Exhibits homogeneity, good pore size and in general good physical appearance. | |
| | | Sodium Bicarbonate<br>Sodium Chloride | Agitation: 950 rpm<br>Glycerolysis | | | | | |
| | | Glycerin<br>Sodium Hydroxide<br>Phosphoric Acid | Temp = 215° C.<br>Time = 45 mins.<br>Agitation: 1300 rpm | | | | | |
| | 22 | Olein Phase of palm oil<br>Hydrogen Peroxide<br>Formic acid | Epoxidation:<br>Temperature = 50° C.<br>Time: 3 hrs. | # OH = 79.97 mg KOH/g sample | Palm Polyol<br>Diethylene glycol<br>Dibutyltin Dilaureate (DBTDL)<br>Silicone emulsion<br>Methylene diisocyanate (MDI) | Vigorous agitation<br>Ambient temperature | It was found that part of the polyol did not react and remained in the lower part, a white foam being found in the upper part. The reaction time was slow. | |
| | | Sodium Bicarbonate<br>Sodium Chloride | Agitation: 950 rpm<br>Glycerolysis | | | | | |
| | | Glycerin<br>Sodium Hydroxide<br>Phosphoric Acid | Temp = 215° C.<br>Time = 45 mins.<br>Agitation: 1300 rpm | | | | | |
| | 23 | Olein Phase of palm oil<br>Hydrogen Peroxide<br>Formic acid | Epoxidation<br>Temperature = 50° C.<br>Time: 3 hrs. | # OH = 263.4 mg KOH/g sample | Palm Polyol<br>1,6 butanediol (BDO)<br>Dibutyltin Dilaureate (DBTDL)<br>Silicone 193C<br>Methylene diisocyanate (MDI) | Vigorous agitation<br>Ambient temperature | This polyurethane presents good features, compared with that of the same Hydroxil number, with DEG, however, its rigidity is less. | |
| | | Sodium Bicarbonate<br>Sodium Chloride | Agitation: 950 rpm<br>Glycerolysis | | | | | |
| | | Glycerin<br>Sodium Hydroxide<br>Phosphoric Acid | Temp = 180° C.<br>Time = 25 mins.<br>Agitation: 1300 rpm | | | | | |
| | 24 | Olein Phase of palm oil<br>Hydrogen Peroxide<br>Formic acid | Epoxidation:<br>Temperature = 50° C.<br>Time: 3 hrs. | # OH = 263.4 mg KOH/g sample | Palm polyol<br>Diethylene glycol<br>Dibutyltin Dilaureate (DBTDL) | Vigorous agitation<br>Ambient temperature | This polyurethane exhibits good features, it is a semi-rigid product. | |
| | | Sodium Bicarbonate<br>Sodium Chloride | Agitation: 950 rpm<br>Glycerolysis | | | | | |
| | | Glycerin<br>Sodium Hydroxide<br>Phosphoric Acid | Temp = 180° C.<br>Time = 25 mins.<br>Agitation: 1300 rpm | | | | | |
| | 25 | Olein Phase of palm oil | Epoxidation | # OH = 263.4 mg KOH/g sample | Palm Polyol | Vigorous agitation | Shows good replicability and is | Density = 0.133 g/cm3 |

-continued

| Route | Experiment No. | Preparation of polyol | | | Preparation of Polyurethane | | | |
|---|---|---|---|---|---|---|---|---|
| | | Reagents | Operational conditions | Evaluation Results | Reagents | Operational conditions | Product Features | Evaluation Results |
| | | Hydrogen Peroxide Formic acid | Temperature = 50° C. Time: 3 hrs. | | Diethylene glycol Dibutyltin Dilaureate (DBTDL) Silicone 193C Methylene diisocyanate (MDI) | Ambient temperature | sent for the characterization by density test. | |
| | | Sodium Bicarnonate Sodium Chloride | Agitation: 950 rpm Glycerolysis | | | | | |
| | | Glycerin Sodium Hydroxide Phosphoric Acid | Temp = 180° C. Time = 25 mins. Agitation: 1300 rpm | | | | | |
| | 26 | Olein Phase of palm oil | Epoxidation: | # OH = 263.4 mg KOH/g sample | Palm polyol | Vigorous agitation | Exhibits good replicability and is sent for the test by characterization of compression. | Young module = 1.32276 Mpa Maximu effort = 0.08760 Mpa |
| | | Hydrogen Peroxide Formic acid | Temperature = 50° C. Time: 3 hrs. | | Diethylene glycol Dibutyltin Dilaureate (DBTDL) Silicone 193C Methylene diisocyanate (MDI) | Ambient temperature | | |
| | | Sodium Bicarnonate Sodium Chloride | Agitation: 950 rpm Glycerolysis | | | | | |
| | | Glycerin Sodium Hydroxide Phosphoric Acid | Temp = 180° C. Time = 25 mins. Agitation: 1300 rpm | | | | | |
| | 27 | Olein Phase of palm oil | Epoxidation | # OH = 437.66 mg KOH/g sample | Palm Polyol | Vigorous agitation | Polymer with a small pore size and good velocity features. Chosen for the rank of PU characterization by density. | Density = 0.450 g/cm3 |
| | | Hydrogen Peroxide Formic acid | Temperature = 50° C. Time: 3 hrs. | | Diethylene glycol Dibutyltin Dilaureate (DBTDL) Silicone 193C Methylene diisocyanate (MDI) | Ambient temperature | | |
| | | Sodium Bicarnonate Sodium Chloride | Agitation: 950 rpm Glycerolysis | | | | | |
| | | Glycerin Sodium Hydroxide Phosphoric Acid | Temp = 215° C. Time = 45 mins. Agitation: 1300 rpm | | | | | |

The invention claimed is:

1. A method for the production of polyol from palm oil, characterized by comprising the following steps:
   a. mixing a source of palm oil with formic acid in the presence of heat;
   b. adding hydrogen peroxide to the mixture of step a) and shake to obtain a reaction product of step b);
   c. washing the reaction product of step b) with water at a temperature between 55° C. and 65° C. to obtain a product of step c);
   d. washing the product obtained in the step c) with 5% sodium bicarbonate to obtain a product of reaction of step d);
   e. washing the product of reaction of step d) with water at a temperature between 55° C. and 65° C. to obtain a product of step e);
   f. washing the product obtained in step e) with 5% sodium chloride to obtain an aqueous phase and an organic phase;
   g. discarding the aqueous phase obtained in step f) to obtain an epoxidized oil;
   h. mixing the epoxidized oil obtained in step g) with glycerol and a catalyst, in the presence of heat and agitation, wherein the catalyst is sodium hydroxide;
   i. neutralizing the sodium hydroxide catalyst with drops of phosphoric acid to avoid the formation of soap; and
   j. obtaining the polyol resulting in a hydroxyl number between 400 and 440 mg KOH/g sample,
   wherein step h) has a reaction temperature that varies between 170° C. and 190° C. and has a time of reaction that varies between 40 and 50 minutes.

2. The method in accordance with claim 1, wherein the source of palm oil in step a) is the olein phase of crude palm oils.

3. The method in accordance with claim 1, wherein the source of palm oil in step a) is the olein phase of refined bleached and deodorized palm oil (RBD).

4. The method in accordance with claim 1, wherein step b) has a reaction temperature that varies between 45° C. and 55° C. and has a time of reaction that varies between 1 and 2 hours after the addition of hydrogen peroxide.

* * * * *